(12) United States Patent
Johnson et al.

(10) Patent No.: US 7,267,677 B2
(45) Date of Patent: Sep. 11, 2007

(54) VESSEL SEALING INSTRUMENT

(75) Inventors: Kristin D. Johnson, Louisville, CO (US); Chris J. Ehr, Longmont, CO (US); Gene H. Arts, Berthoud, CO (US)

(73) Assignee: Sherwood Services AG, Schaffhausen (CH)

( * ) Notice: Subject to any disclaimer, the term of this patent is extended or adjusted under 35 U.S.C. 154(b) by 163 days.

(21) Appl. No.: 10/284,562

(22) Filed: Oct. 30, 2002

(65) Prior Publication Data

US 2003/0199869 A1 Oct. 23, 2003

Related U.S. Application Data

(63) Continuation-in-part of application No. 10/116,824, filed on Apr. 5, 2002, now abandoned, which is a continuation-in-part of application No. PCT/US01/11420, filed on Apr. 6, 2001, which is a continuation-in-part of application No. 09/425,696, filed on Oct. 22, 1999, now Pat. No. 6,511,480, which is a continuation-in-part of application No. 09/178,027, filed on Oct. 23, 1998, now Pat. No. 6,277,117.

(51) Int. Cl.
    *A61B 18/14* (2006.01)
(52) U.S. Cl. .......................... 606/51; 606/171
(58) Field of Classification Search .................. 606/39, 606/40, 41, 45, 46, 47, 48, 49, 50, 51, 52
    See application file for complete search history.

(56) References Cited

U.S. PATENT DOCUMENTS

| | | |
|---|---|---|
| 0,371,664 A | 10/1887 | Brannan et al. |
| 0,702,472 A | 6/1902 | Pignolet |
| 0,728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |

(Continued)

FOREIGN PATENT DOCUMENTS

CA 2104423 2/1994

(Continued)

OTHER PUBLICATIONS

"Innovations in Electrosurgery" Sales/Product Literature.

(Continued)

*Primary Examiner*—Lee S. Cohen

(57) ABSTRACT

A bipolar electrosurgical instrument for clamping, grasping, manipulating, and sealing tissue includes first and second shafts each having a jaw member extending from a distal end thereof and a handle disposed at a proximal end thereof. The handle being operable to effect movement of the jaw members relative to one another from a first position wherein the jaw members are disposed in spaced relation relative to one another to a second position wherein the jaw members cooperate to grasp tissue therebetween. The bipolar instrument is connectable to a source of electrical energy having a first electrical potential connected to one of the jaw members and a second electrical potential connected to the other of the jaw members such that the jaw members are capable of selectively conducting energy through tissue held therebetween to effect a seal. Both the first and second electrical potentials are transmitted to the jaw members through the first shaft.

19 Claims, 17 Drawing Sheets

U.S. PATENT DOCUMENTS

| | | |
|---|---|---|
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,127,222 A | 11/1978 | Adams |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |

| | | | | | | |
|---|---|---|---|---|---|---|
| 5,611,798 A | 3/1997 | Eggers | | 5,984,939 A | 11/1999 | Yoon |
| 5,626,578 A | 5/1997 | Tihon | | 5,989,277 A | 11/1999 | LeMaire, III et al. |
| 5,626,609 A | 5/1997 | Zvenyatsky et al. | | 6,004,335 A | 12/1999 | Vaitekunas et al. |
| 5,630,833 A | 5/1997 | Katsaros et al. | | 6,010,516 A | 1/2000 | Hulka et al. |
| 5,637,110 A | 6/1997 | Pennybacker et al. | | 6,024,741 A | 2/2000 | Willaimson et al. |
| 5,643,294 A | 7/1997 | Tovey et al. | | 6,024,744 A | 2/2000 | Kese et al. |
| 5,647,869 A | 7/1997 | Goble et al. | | 6,030,384 A | 2/2000 | Nezhat |
| 5,649,959 A | 7/1997 | Hannam et al. | | 6,033,399 A | 3/2000 | Gines |
| 5,658,281 A | 8/1997 | Heard | | 6,039,733 A | 3/2000 | Buysse et al. |
| 5,662,667 A | 9/1997 | Knodel | | 6,041,679 A | 3/2000 | Slater et al. |
| 5,665,100 A | 9/1997 | Yoon | | 6,050,996 A | 4/2000 | Schmaltz et al. |
| 5,667,526 A | 9/1997 | Levin | | 6,053,914 A | 4/2000 | Eggers et al. |
| 5,674,220 A | 10/1997 | Fox et al. | | 6,053,933 A | 4/2000 | Balazs et al. |
| 5,681,282 A | 10/1997 | Eggers et al. | | D424,694 S | 5/2000 | Tetzlaff et al. |
| 5,693,051 A | 12/1997 | Schulze et al. | | D425,201 S | 5/2000 | Tetzlaff et al. |
| 5,695,522 A | 12/1997 | LeMaire, III et al. | | 6,059,782 A | 5/2000 | Novak et al. |
| 5,700,261 A | 12/1997 | Brinkerhoff | | RE36,795 E | 7/2000 | Rydell |
| 5,702,390 A | 12/1997 | Austin et al. | | 6,083,223 A | 7/2000 | Baker |
| 5,707,369 A | 1/1998 | Vaitekunas et al. | | 6,086,586 A | 7/2000 | Hooven |
| 5,709,680 A | 1/1998 | Yates et al. | | 6,090,107 A | 7/2000 | Borgmeier et al. |
| 5,716,366 A | 2/1998 | Yates | | 6,096,037 A * | 8/2000 | Mulier et al. .................. 606/49 |
| 5,727,428 A | 3/1998 | LeMaire, III et al. | | 6,099,550 A | 8/2000 | Yoon |
| 5,735,848 A | 4/1998 | Yates et al. | | 6,102,909 A | 8/2000 | Chen et al. |
| 5,743,906 A | 4/1998 | Parins et al. | | 6,110,171 A | 8/2000 | Rydell |
| 5,755,717 A | 5/1998 | Yates et al. | | 6,113,596 A | 9/2000 | Hooven et al. |
| 5,766,130 A | 6/1998 | Selmonosky | | 6,113,598 A | 9/2000 | Baker |
| 5,766,166 A | 6/1998 | Hooven | | 6,117,158 A | 9/2000 | Measamer et al. |
| 5,766,170 A | 6/1998 | Eggers | | 6,123,701 A | 9/2000 | Nezhat |
| 5,769,849 A | 6/1998 | Eggers | | H1904 H | 10/2000 | Yates et al. |
| 5,772,655 A | 6/1998 | Bauer et al. | | 6,126,658 A | 10/2000 | Baker |
| 5,772,670 A | 6/1998 | Brosa | | 6,152,923 A | 11/2000 | Ryan |
| 5,776,128 A | 7/1998 | Eggers | | 6,162,220 A | 12/2000 | Nezhat |
| 5,776,130 A | 7/1998 | Buysse et al. | | 6,174,309 B1 * | 1/2001 | Wrublewski et al. ......... 606/45 |
| 5,779,701 A | 7/1998 | McBrayer et al. | | 6,179,834 B1 | 1/2001 | Buysse et al. |
| 5,792,137 A | 8/1998 | Carr et al. | | 6,179,837 B1 | 1/2001 | Hooven |
| 5,792,177 A | 8/1998 | Kaseda | | 6,183,467 B1 | 2/2001 | Shapeton et al. |
| 5,797,938 A | 8/1998 | Paraschac et al. | | 6,187,003 B1 | 2/2001 | Buysse et al. |
| 5,797,958 A | 8/1998 | Yoon | | 6,190,386 B1 | 2/2001 | Rydell |
| 5,800,449 A | 9/1998 | Wales | | 6,193,718 B1 | 2/2001 | Kortenbach et al. |
| 5,807,393 A | 9/1998 | Williamson, IV et al. | | 6,206,877 B1 | 3/2001 | Kese et al. |
| 5,810,808 A | 9/1998 | Eggers | | 6,217,602 B1 | 4/2001 | Redmon |
| 5,810,811 A | 9/1998 | Yates et al. | | 6,224,593 B1 | 5/2001 | Ryan et al. |
| 5,810,877 A | 9/1998 | Roth et al. | | 6,228,080 B1 | 5/2001 | Gines |
| 5,814,043 A | 9/1998 | Shapeton | | 6,228,083 B1 | 5/2001 | Lands et al. |
| 5,820,630 A | 10/1998 | Lind | | 6,267,761 B1 | 7/2001 | Ryan |
| 5,827,271 A | 10/1998 | Buysse et al. | | 6,270,497 B1 | 8/2001 | Sekino et al. |
| 5,827,279 A | 10/1998 | Hughett et al. | | 6,270,508 B1 | 8/2001 | Klieman et al. |
| 5,827,281 A | 10/1998 | Levin | | 6,273,887 B1 | 8/2001 | Yamauchi et al. |
| 5,833,690 A | 11/1998 | Yates et al. | | 6,277,117 B1 | 8/2001 | Tetzlaff et al. |
| 5,843,080 A | 12/1998 | Fleenor et al. | | 6,280,458 B1 | 8/2001 | Boche et al. |
| 5,849,022 A | 12/1998 | Sakashita et al. | | 6,283,961 B1 | 9/2001 | Underwood et al. |
| 5,853,412 A | 12/1998 | Mayenberger | | D449,886 S | 10/2001 | Tetzlaff et al. |
| 5,860,976 A | 1/1999 | Billings et al. | | 6,322,561 B1 | 11/2001 | Eggers et al. |
| 5,876,401 A | 3/1999 | Schulze et al. | | 6,334,861 B1 | 1/2002 | Chandler et al. |
| 5,891,141 A | 4/1999 | Rydell | | 6,350,264 B1 | 2/2002 | Hooven |
| 5,891,142 A * | 4/1999 | Eggers et al. .................. 606/51 | | 6,352,536 B1 | 3/2002 | Buysse et al. |
| 5,893,863 A | 4/1999 | Yoon | | D457,958 S | 5/2002 | Dycus et al. |
| 5,893,875 A | 4/1999 | Oconnor et al | | D457,959 S | 5/2002 | Tetzlaff et al. |
| 5,893,877 A | 4/1999 | Gampp, Jr. et al. | | 6,387,094 B1 | 5/2002 | Eitenmuller |
| 5,902,301 A | 5/1999 | Olig | | 6,398,779 B1 | 6/2002 | Buysse et al. |
| 5,906,630 A | 5/1999 | Anderhub et al. | | 6,402,747 B1 | 6/2002 | Lindemann et al. |
| 5,908,420 A | 6/1999 | Parins et al. | | 6,409,728 B1 | 6/2002 | Ehr et al. |
| 5,911,719 A | 6/1999 | Eggers | | H2037 H | 7/2002 | Yates et al. |
| 5,913,874 A | 6/1999 | Berns et al. | | 6,419,675 B1 * | 7/2002 | Gallo, Sr. .................... 606/46 |
| 5,921,984 A | 7/1999 | Sutcu et al. | | 6,443,952 B1 | 9/2002 | Mulier et al. |
| 5,925,043 A | 7/1999 | Kumar et al. | | 6,443,970 B1 | 9/2002 | Schulze et al. |
| 5,935,126 A | 8/1999 | Riza | | 6,451,018 B1 | 9/2002 | Lands et al. |
| 5,944,718 A | 8/1999 | Austin et al. | | 6,458,128 B1 | 10/2002 | Schulze |
| 5,951,549 A | 9/1999 | Richardson et al. | | 6,458,130 B1 | 10/2002 | Frazier et al. |
| 5,954,720 A | 9/1999 | Wilson et al. | | 6,464,701 B1 | 10/2002 | Hooven et al. |
| 5,957,923 A | 9/1999 | Hahnen et al. | | 6,511,480 B1 | 1/2003 | Tetzlaff et al. |
| 5,961,514 A | 10/1999 | Long et al. | | 6,585,735 B1 | 7/2003 | Frazier et al. |
| 5,976,132 A | 11/1999 | Morris | | 6,620,161 B2 | 9/2003 | Schulze et al. |

| | | | | | | |
|---|---|---|---|---|---|---|
| 6,652,521 B2 | 11/2003 | Schulze | | 2005/0119655 A1 | 6/2005 | Moses et al. |
| 6,656,177 B2 | 12/2003 | Truckai et al. | | 2005/0149151 A1 | 7/2005 | Orszulak et al. |
| 6,669,696 B2 | 12/2003 | Bacher et al. | | 2006/0064085 A1 | 3/2006 | Schechter et al. |
| 6,682,528 B2 | 1/2004 | Frazier et al. | | 2006/0079891 A1 | 4/2006 | Arts et al. |
| 6,685,724 B1 | 2/2004 | Haluck | | 2006/0129146 A1 | 6/2006 | Dycus et al. |
| 6,726,068 B2 | 4/2004 | Miller | | 2006/0161150 A1 | 7/2006 | Keppel |
| 6,733,498 B2 | 5/2004 | Paton et al. | | 2006/0167450 A1 | 7/2006 | Johnson et al. |
| 6,743,229 B2 | 6/2004 | Buysse et al. | | 2006/0167452 A1 | 7/2006 | Moses et al. |
| 6,770,072 B1 | 8/2004 | Truckai et al. | | 2006/0173452 A1 | 8/2006 | Buysse et al. |
| 6,773,434 B2 | 8/2004 | Ciarrocca | | 2006/0189980 A1 | 8/2006 | Johnson et al. |
| 6,776,780 B2 | 8/2004 | Mulier et al. | | 2006/0189981 A1 | 8/2006 | Dycus et al. |
| D496,997 S | 10/2004 | Dycus et al. | | 2006/0190035 A1 | 8/2006 | Hushka et al. |
| 6,802,843 B2 | 10/2004 | Truckai et al. | | 2006/0217709 A1 | 9/2006 | Couture et al. |
| D499,181 S | 11/2004 | Dycus et al. | | 2006/0224158 A1 | 10/2006 | Odom et al. |
| 6,818,000 B2 | 11/2004 | Muller et al. | | | | |
| 6,926,716 B2 | 8/2005 | Baker et al. | | FOREIGN PATENT DOCUMENTS | | |
| 6,929,644 B2 | 8/2005 | Truckai et al. | | DE | 2415263 | 10/1975 |
| 6,932,810 B2 | 8/2005 | Ryan | | DE | 8712328 | 3/1988 |
| 6,942,662 B2 | 9/2005 | Goble et al. | | DE | 29616210 | 1/1997 |
| 6,964,662 B2 | 11/2005 | Kidooka | | DE | 19608716 | 4/1997 |
| 7,033,354 B2 | 4/2006 | Keppel | | DE | 19751108 | 5/1999 |
| 7,083,618 B2 | 8/2006 | Couture et al. | | EP | 0364216 A1 | 4/1990 |
| 7,090,673 B2 | 8/2006 | Dycus et al. | | EP | 518230 A1 | 12/1992 |
| 7,101,371 B2 | 9/2006 | Dycus et al. | | EP | 0 541 930 B1 | 5/1993 |
| 7,101,372 B2 | 9/2006 | Dycus et al. | | EP | 0572131 A1 | 12/1993 |
| 7,101,373 B2 | 9/2006 | Dycus et al. | | EP | 584787 A1 | 3/1994 |
| 7,103,947 B2 | 9/2006 | Sartor et al. | | EP | 0623316 A1 | 11/1994 |
| 7,118,570 B2 | 10/2006 | Tetzlaff et al. | | EP | 0624348 A2 | 11/1994 |
| 7,118,587 B2 | 10/2006 | Dycus et al. | | EP | 0650701 A1 | 5/1995 |
| 2002/0013583 A1 | 1/2002 | Camran et al. | | EP | 0694290 A3 | 3/1996 |
| 2002/0099372 A1 | 7/2002 | Schulze et al. | | EP | 0717966 A1 | 6/1996 |
| 2002/0107517 A1 | 8/2002 | Witt et al. | | EP | 0754437 A3 | 3/1997 |
| 2002/0111624 A1 | 8/2002 | Witt et al. | | EP | 853922 A1 | 7/1998 |
| 2002/0188294 A1 | 12/2002 | Couture et al. | | EP | 0875209 A1 | 11/1998 |
| 2003/0018331 A1 | 1/2003 | Dycus et al. | | EP | 0878169 A1 | 11/1998 |
| 2003/0069571 A1 | 4/2003 | Treat et al. | | EP | 0887046 A3 | 1/1999 |
| 2003/0078578 A1 | 4/2003 | Truckai et al. | | EP | 0923907 A1 | 6/1999 |
| 2003/0139741 A1 | 7/2003 | Goble et al. | | EP | 0988990 A1 | 3/2000 |
| 2003/0139742 A1 | 7/2003 | Wampler et al. | | EP | 1034747 A1 | 9/2000 |
| 2003/0158549 A1 | 8/2003 | Swanson | | EP | 1034748 A1 | 9/2000 |
| 2003/0199869 A1 | 10/2003 | Johnson et al. | | EP | 1025807 A3 | 10/2000 |
| 2003/0216732 A1 | 11/2003 | Truckai et al. | | EP | 1034746 A3 | 10/2000 |
| 2003/0220637 A1 | 11/2003 | Truckai et al. | | EP | 1050278 A1 | 11/2000 |
| 2003/0236325 A1 | 12/2003 | Bonora | | EP | 1053719 A1 | 11/2000 |
| 2004/0030330 A1 | 2/2004 | Brassell et al. | | EP | 1053720 A1 | 11/2000 |
| 2004/0030332 A1 | 2/2004 | Knowlton et al. | | EP | 1055399 A1 | 11/2000 |
| 2004/0049185 A1 | 3/2004 | Latterell et al. | | EP | 1055400 A1 | 11/2000 |
| 2004/0116979 A1 | 6/2004 | Truckai et al. | | EP | 1080694 A1 | 3/2001 |
| 2004/0147925 A1 | 7/2004 | Buysse et al. | | EP | 1082944 A1 | 3/2001 |
| 2004/0225288 A1 | 11/2004 | Buysse et al. | | EP | 1159926 A2 | 12/2001 |
| 2004/0230189 A1 | 11/2004 | Keppel | | EP | 1301135 A | 4/2003 |
| 2004/0236325 A1 | 11/2004 | Tetzlaff et al. | | EP | 1330991 A1 | 7/2003 |
| 2004/0243125 A1 | 12/2004 | Dycus et al. | | EP | 1486177 A2 | 6/2004 |
| 2004/0249371 A1 | 12/2004 | Dycus et al. | | EP | 1532932 A1 | 5/2005 |
| 2004/0249374 A1 | 12/2004 | Tetzlaff et al. | | EP | 1707143 A1 | 4/2006 |
| 2004/0250419 A1 | 12/2004 | Sremcich et al | | GB | 2214430 A | 6/1989 |
| 2004/0254573 A1 | 12/2004 | Dycus et al. | | JP | 501068 | 9/1984 |
| 2005/0004564 A1 | 1/2005 | Wham et al. | | JP | 502328 | 3/1992 |
| 2005/0004568 A1 | 1/2005 | Lawes et al. | | JP | 5-40112 | 2/1993 |
| 2005/0004570 A1 | 1/2005 | Chapman et al. | | JP | 06343644 A2 | 12/1994 |
| 2005/0021025 A1 | 1/2005 | Buysse et al. | | JP | 07265328 A2 | 10/1995 |
| 2005/0021026 A1 | 1/2005 | Baily | | JP | 08056955 A2 | 3/1996 |
| 2005/0021027 A1 | 1/2005 | Shields et al. | | JP | 08252263 A2 | 10/1996 |
| 2005/0033278 A1 | 2/2005 | McClurken et al. | | JP | 09010223 A2 | 1/1997 |
| 2005/0101951 A1 | 5/2005 | Wham et al. | | JP | 11244298 A2 | 9/1999 |
| 2005/0101952 A1 | 5/2005 | Lands et al. | | JP | 2000342599 A2 | 12/2000 |
| 2005/0107784 A1 | 5/2005 | Moses et al. | | JP | 2000350732 A2 | 12/2000 |
| 2005/0107785 A1 | 5/2005 | Dycus et al. | | JP | 2001008944 A2 | 1/2001 |
| 2005/0113818 A1 | 5/2005 | Sartor et al. | | JP | 2001029356 A2 | 2/2001 |
| 2005/0113819 A1 | 5/2005 | Wham et al. | | JP | 2001128990 A2 | 5/2001 |
| 2005/0113826 A1 | 5/2005 | Johnson et al. | | SU | 401367 | 11/1974 |
| 2005/0113827 A1 | 5/2005 | Dumbauld et al. | | WO | WO89/00757 | 1/1989 |
| 2005/0113828 A1 | 5/2005 | Shields et al. | | | | |

| | | |
|---|---|---|
| WO | WO92/06642 | 4/1992 |
| WO | WO 92/06642 | 4/1992 |
| WO | WO94/08524 A | 4/1994 |
| WO | WO94/20025 | 9/1994 |
| WO | WO 95/02369 | 1/1995 |
| WO | WO95/02369 | 1/1995 |
| WO | WO95/07662 | 3/1995 |
| WO | WO96/22056 | 7/1996 |
| WO | WO96/13218 | 9/1996 |
| WO | WO97/00646 | 1/1997 |
| WO | WO 97/00646 | 1/1997 |
| WO | WO97/00647 | 1/1997 |
| WO | WO 97/00647 | 1/1997 |
| WO | WO97/10764 | 3/1997 |
| WO | WO 97/24073 | 7/1997 |
| WO | WO97/24073 | 7/1997 |
| WO | WO 97/24993 | 7/1997 |
| WO | WO97/24993 | 7/1997 |
| WO | WO 98/27880 | 7/1998 |
| WO | WO98/27880 | 7/1998 |
| WO | WO99/03407 | 1/1999 |
| WO | WO 99/03407 | 1/1999 |
| WO | WO 99/03408 | 1/1999 |
| WO | WO99/03408 | 1/1999 |
| WO | WO99/03409 | 1/1999 |
| WO | WO 99/03409 | 1/1999 |
| WO | WO99/12488 A | 3/1999 |
| WO | WO99/40857 | 8/1999 |
| WO | WO99/40861 | 8/1999 |
| WO | WO99/51158 | 10/1999 |
| WO | WO 99/51158 | 10/1999 |
| WO | WO99/66850 | 12/1999 |
| WO | WO99/66850 A | 12/1999 |
| WO | WO 00/24330 | 5/2000 |
| WO | WO00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 A1 | 8/2001 |
| WO | WO02/07627 | 1/2002 |
| WO | WO02/060783 | 10/2002 |
| WO | WO02/080784 | 10/2002 |
| WO | WO02/080785 | 10/2002 |
| WO | WO02/080786 | 10/2002 |
| WO | WO02/080793 | 10/2002 |
| WO | WO02/080794 | 10/2002 |
| WO | WO 02/080795 | 10/2002 |
| WO | WO 02/080796 | 10/2002 |
| WO | WO 02/080796 A1 | 10/2002 |
| WO | WO02/080797 | 10/2002 |
| WO | WO 02/080798 | 10/2002 |
| WO | WO 02/080799 | 10/2002 |
| WO | WO02/081170 | 10/2002 |
| WO | WO 03/101311 | 12/2003 |
| WO | WO2004/032777 | 4/2004 |
| WO | WO 2004/052221 A1 | 6/2004 |
| WO | WO2004/073490 | 9/2004 |
| WO | WO2004/073753 | 9/2004 |
| WO | WO2004/082495 | 9/2004 |
| WO | WO 2004/082495 A1 | 9/2004 |
| WO | WO 2004/098383 A1 | 11/2004 |
| WO | WO2004/103156 | 12/2004 |

OTHER PUBLICATIONS

LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp.569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3.
E. David Crawford "Use of a Novel Vessel Sealing Technology in Management of the Dorsal Veinous Complex" Sales Product Literature.
Jarrett et al., "Use of the LigaSure Vessel Sealing System for Peri-Hilar Vessels in Laparoscopic Nephrectomy" Sales Product Literature.
E. David Crawford "Evaluation of a New Vessel Sealing Device in Urologic Cancer Surgery" Sales Product Literature.
Joseph Ortenberg "LigaSure System Used in Laparoscopic 1st and 2nd Stage Orchiopexy" Innovations That Work, Nov. 2002.
Koyte et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales Product Literature.
Johnson et al. "Evaluation of a Bipolar electrothermal Vessel Sealing Device in Hemorrhoidectomy" Sales Product Literature.
PCT/US01/11340 International Search Report.
PCT/US01/11420 International Search Report.
PCT/US02/01890 International Search Report.
PCT/US02/11100 International Search Report.
PCT/US04/03436 International Search Report.
PCT/US04/13273 International Search Report.
PCT/US04/15311 International Search Report.
EP 98944778 International Search Report.
EP 98958575 International Search Report.
EP 04027479 International Search Report.
EP 04027705 International Search Report.
EP 04027314 International Search Report.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.

Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J. Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy; A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
Int'l Search Report PCT/US01/11218 dated Aug. 3, 2001.
Int'l Search Report PCT/US99/24869 dated Feb. 3, 2000.
Int'l Search Report PCT/US98/18640 dated Dec. 17, 1998.
Int'l Search Report PCT/US98/23950 dated Dec. 29, 1998.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Johnson et al. "Evaluation of the LigaSure Vessel Sealing System in Hemorrhoidectorrny" American College of Surgeons (ACS) Clinicla Congress Poster (2000).
McLellan et al. "Vessel Sealing for Hemostasis During Pelvic Surgery" Int'l Federation of Gynecology and Obstetrics FIGO World Congress 2000, Washington, D.C.
US 6,090,109, 07/2000, Lands et al. (withdrawn)

* cited by examiner

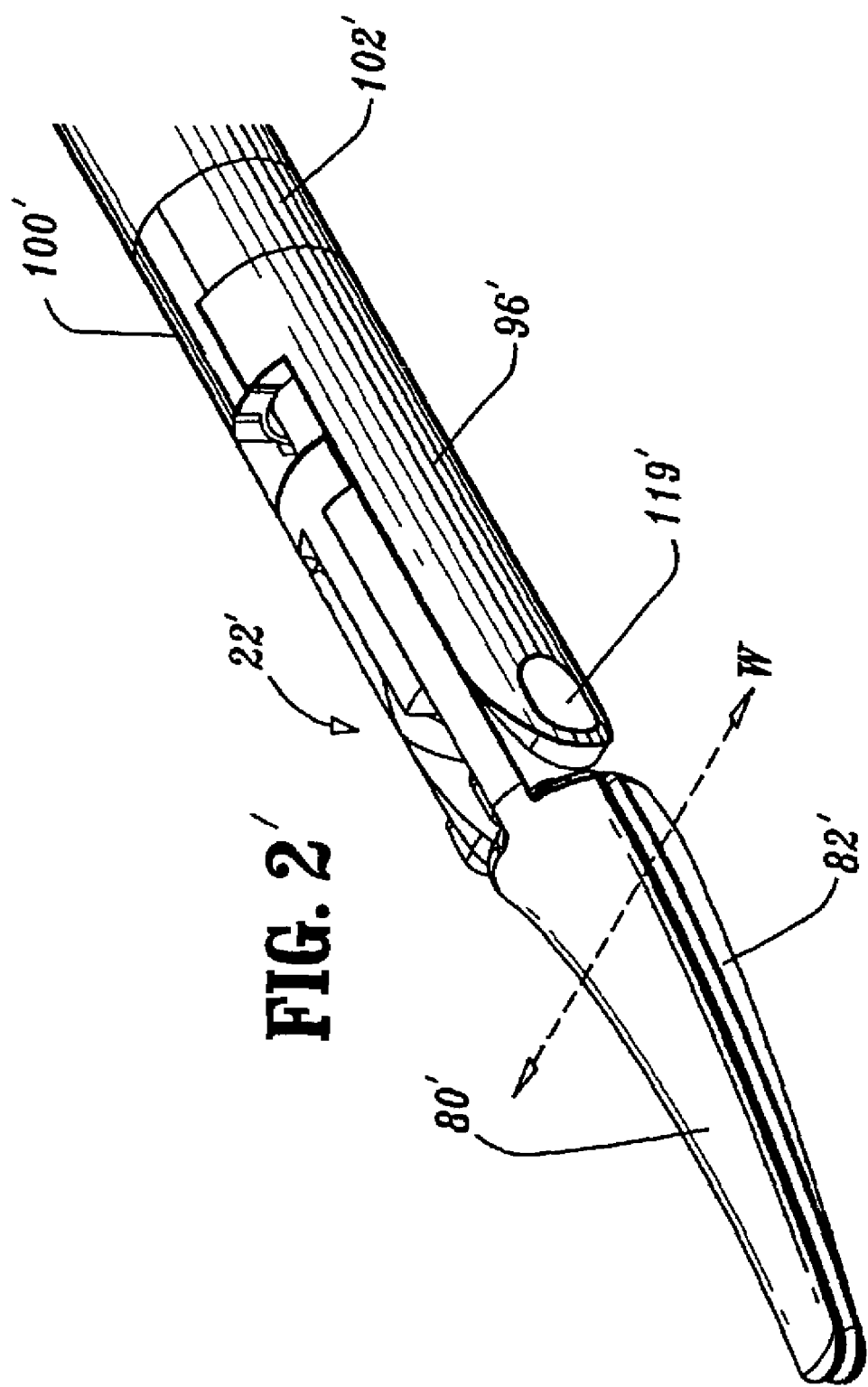

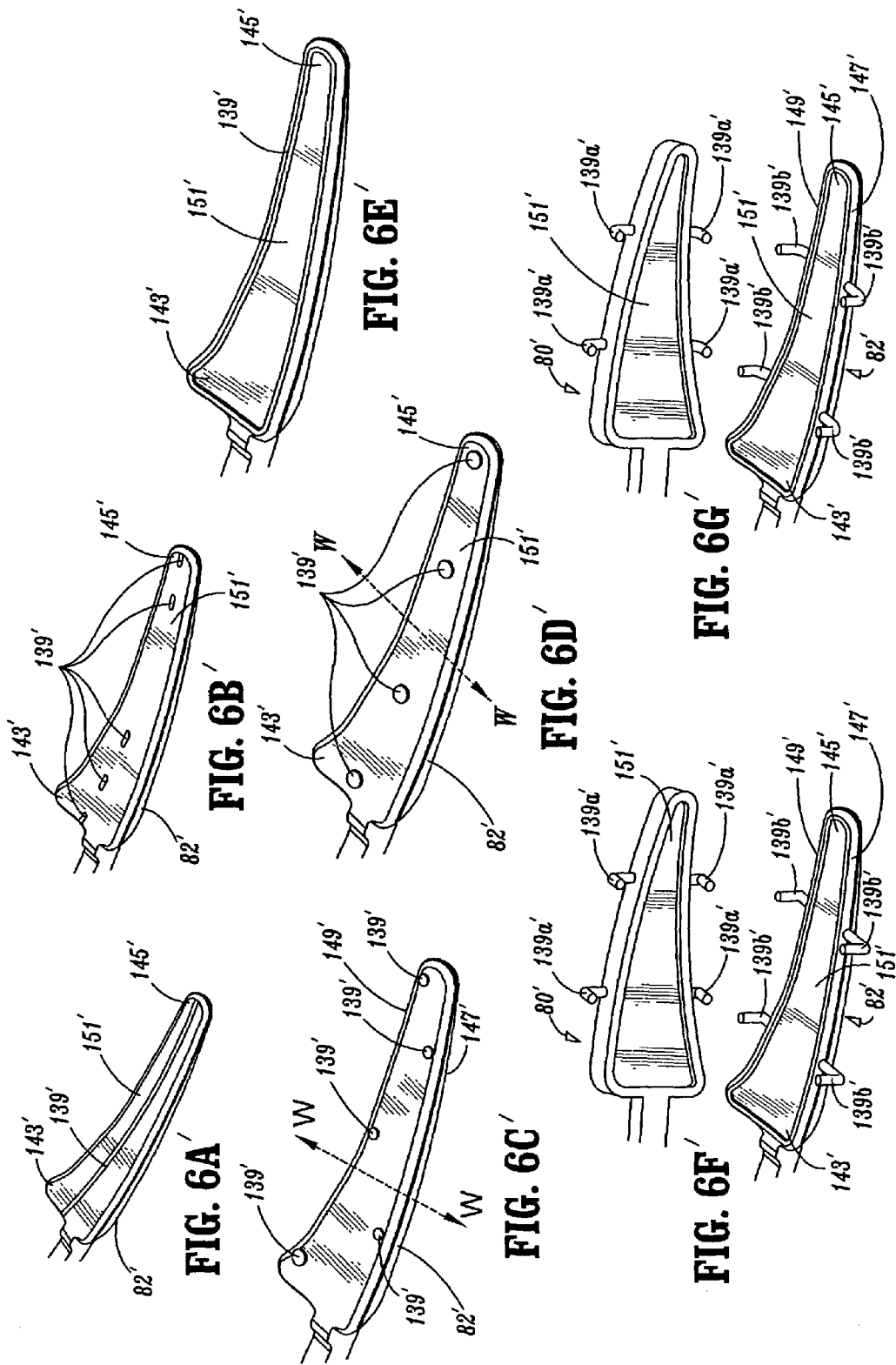

VESSEL SEALING INSTRUMENT

CROSS REFERENCE TO RELATED APPLICATIONS

This application is a continuation-in-part of U.S. application Ser. No. 10/116,824 filed on Apr. 5, 2002, now abandoned, by Tetzlaff et al. which is a continuation-in-part of PCT Application Ser. No. PCT/US01/11420 filed on Apr. 6, 2001 which is a continuation-in-part of U.S. application Ser. No. 09/425,696 filed Oct. 22, 1999, now U.S. Pat. No. 6,511,480, by Philip Mark Tetzlaff et al. which is a continuation-in-part of U.S. application Ser. No. 09/178,027 filed Oct. 23, 1998, now U.S. Pat. No. 6,277,117, by Philip Mark Tetzlaff et al., the entire contents of each of these applications are hereby incorporated by reference.

BACKGROUND

The present disclosure relates to forceps used for open surgical procedures. More particularly, the present disclosure relates to a forceps which applies a combination of mechanical clamping pressure and electrosurgical current to seal tissue.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between 0.001 and 0.006 inches. Below this range, the seal may shred or tear and above this range the lumens may not be properly or effectively sealed.

With respect to smaller vessel, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the issue during compression and prior to activation.

Thus, a need exists to develop a bipolar forceps which effectively seals vascular tissue and solves the aforementioned problems by providing an instrument which enables a large closure force between the opposing jaws members, reduces the chances of short circuiting the opposing jaws during activation and assists in manipulating, gripping and holding the tissue prior to and during activation.

SUMMARY

The present disclosure relates to a bipolar electrosurgical instrument for use in open surgery which includes first and second shafts one of which is connectable to a source of electrosurgical energy. Each shaft includes a jaw member extending from a distal end thereof and a handle disposed at a proximal end thereof for effecting movement of the jaw members relative to one another from a first, open position wherein the jaw members are disposed in spaced relation relative to one another to a second, closed position wherein the jaw members cooperate to grasp tissue therebetween. The source of electrical energy effects first and second electrical potentials in the respective jaw members such that the jaw members are capable of selectively conducting energy through tissue held therebetween to effect a seal.

Preferably, the first and second electrical potentials are created at the jaw members through the first shaft. For example, in one embodiment, the first electrical potential is transmitted through the first shaft by a lead having a terminal end which electrically interfaces with a distal connector which connects a first jaw member to the first electrical potential. The second electrical potential is transmitted through the first shaft by a tube disposed within the first shaft which connects the second jaw member to the second electrical potential.

The first and second jaw members are connected about a pivot pin. The distal connector is preferably interposed between the jaw members and includes a series of flanges which are dimensioned to prevent the emanation of stray currents from the electrically conductive sealing surfaces of the jaw members during activation.

Preferably, the distal connector includes a spring washer or wave washer which acts as an electrical intermediary between the terminal end and the jaw member. In one embodiment, the spring washer is beveled to enhance the electrical interface between the terminal end and the jaw member, i.e., beveling causes the spring washer to rotate relative the terminal end during movement of the jaw members from the first to second positions which provides a self-cleaning, enhanced running electrical contact between the terminal end and the jaw member.

Preferably, the distal connector is made from an insulative substrate and is disposed between the jaw members for electrically isolating the first and second potentials. In one embodiment, the distal connector includes a first surface having at least one recess defined therein which is dimensioned to receive at least a portion of the terminal end of the lead.

In yet another embodiment, one of the jaw members includes a skirt which is dimensioned to prevent exposure of the terminal end during all angles of operation, i.e., when the jaw members are disposed in the first position, the second position and/or during operative movement therebetween.

The lead preferably includes a inner core made from a solid or multi-strand electrically conductive material, e.g., copper/aluminum wire, which is surrounded by an insulative, non-conductive coating, e.g., plastic. In one embodiment, the terminal or distal end of the electrically conductive material is flattened, i.e., "flat-formed", and is dimensioned to substantially encircle a boss which extends from the surface of the distal connector. Preferably, the boss is designed to electrically insulate the terminal end of the lead from the pivot pin.

In another embodiment, at least one non-conductive stop member is disposed on an electrically conductive sealing surface of one of the jaw members. The stop members are designed to control/regulate the distance, i.e., gap, between the jaw members when tissue is held therebetween during activation.

BRIEF DESCRIPTION OF THE DRAWINGS

Various embodiments of the subject instrument are described herein with reference to the drawings wherein:

FIG. 2' is an enlarged view of the distal end of a bipolar instrument incorporated by reference from a prior disclosure;

FIG. 5' is an enlarged view of a distal end of a bipolar instrument incorporated by reference from a prior disclosure;

FIG. 6A'-6G' are enlarged views of jaw members and stop configurations of a bipolar instrument incorporated by reference from a prior disclosure;

DETAILED DESCRIPTION

Figure 1:
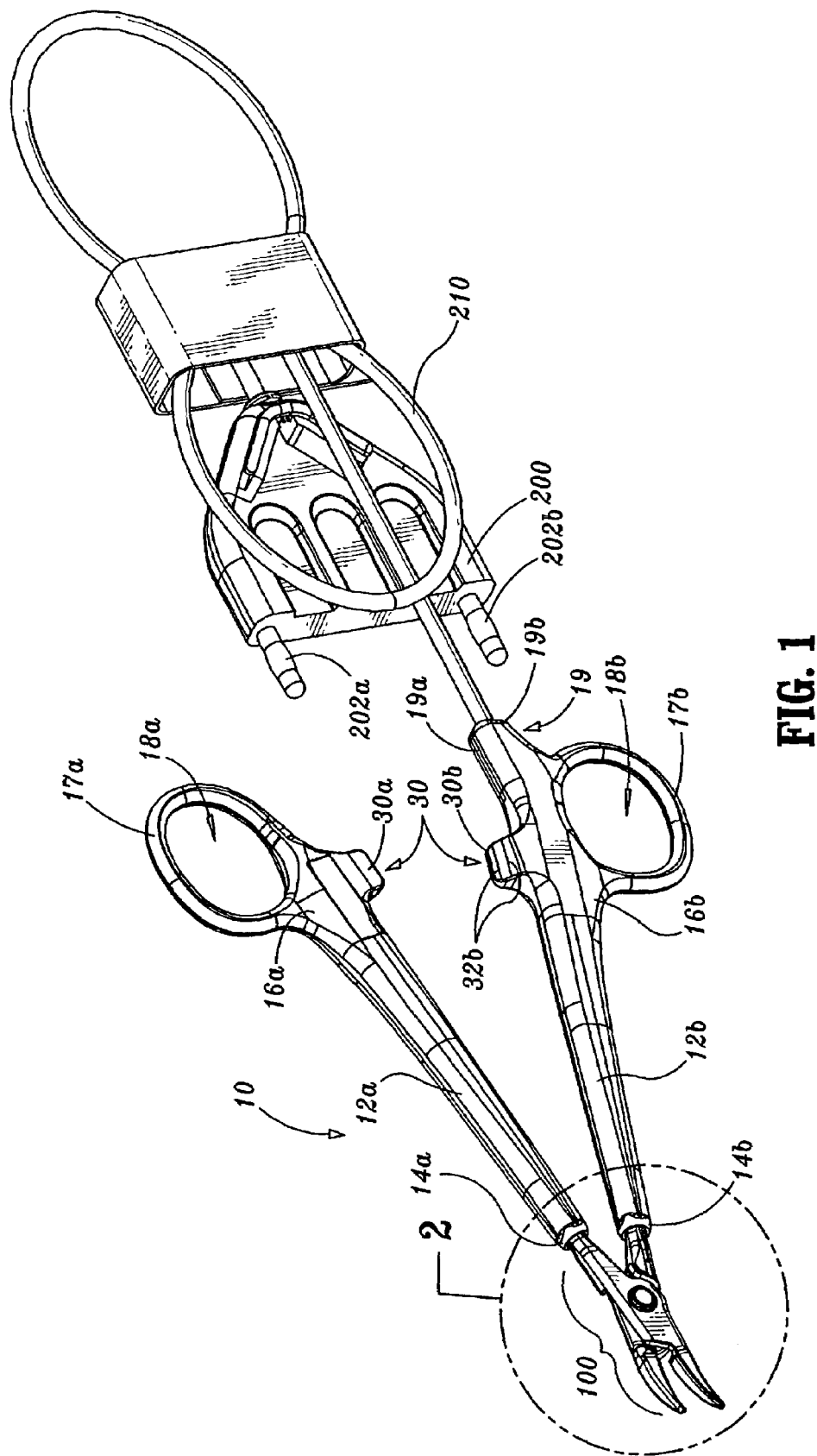
FIG. 1 is a left, perspective view of a forceps according to the present disclosure.

Referring now to FIGS. 1-4, a forceps 10 for use with open surgical procedures includes elongated shaft portions 12a and 12b each having a proximal end 16a and 16b, respectively, and a distal end 14a and 14b, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to distal ends 14a and 14b of shafts 12a and 12b, respectively. As explained in more detail below, the end effector assembly 100 includes pair of opposing jaw members 110 and 120 which are pivotably connected about a pivot pin 150.

Preferably, each shaft 12a and 12b includes a handle 17a and 17b disposed at the proximal end 16a and 16b thereof which each define a finger hole 18a and 18b, respectively, therethrough for receiving a finger of the user. As can be appreciated, finger holes 18a and 18b facilitate movement of the shafts 12a and 12b relative to one another which, in turn, pivot the jaw members 110 and 120 from an open position (FIG. 2) wherein the jaw members 110 and 120 are disposed in spaced relation relative to one another to a clamping or closed position (FIG. 3) wherein the jaw members 110 and 120 cooperate to grasp tissue 400 (FIG. 6) therebetween.

Figure 6:
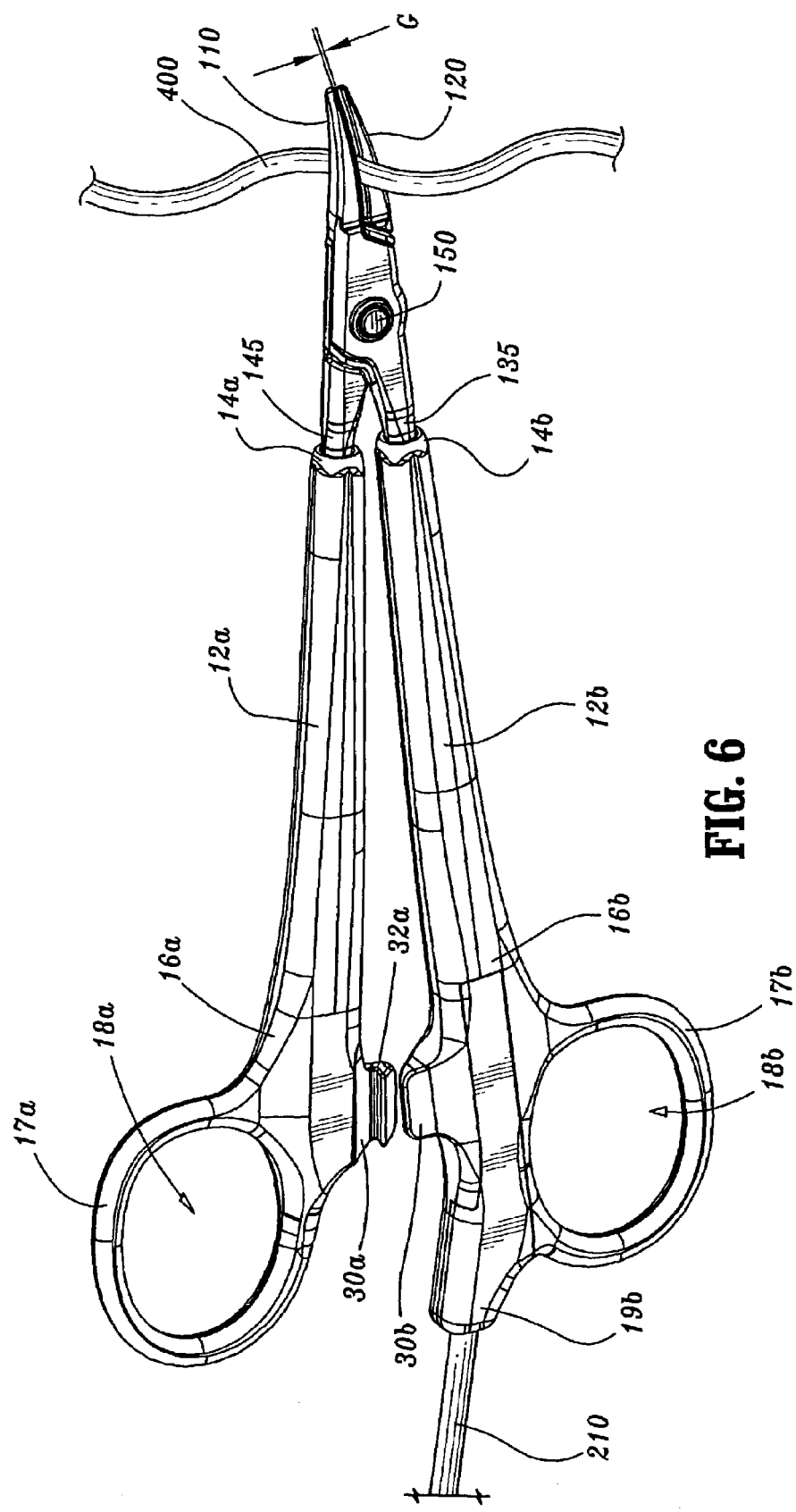
FIG. 6 is a right, perspective view of the forceps of FIG. 1 shown grasping a tissue structure.

A ratchet 30 is preferably included for selectively locking the jaw members 110 and 120 relative to one another at various positions during pivoting. As best shown in FIG. 6, a first ratchet interface, e.g., 30a, extends from the proximal end 16a of shaft member 12a towards a second ratchet interface 30b in a generally vertically aligned manner such that the inner facing surfaces of each ratchet 30a and 30b abut one another upon closure about the tissue 400. Preferably, each ratchet interface 30a and 30b includes a plurality of flanges 32a and 32b, respectively, which projects from the inner facing surface of each ratchet interface 30a and 30b such that the ratchet interfaces 30a and 30b interlock in at least one position. In the embodiment shown in FIG. 6, the ratchet interfaces 30a and 30b interlock at several different positions.

Preferably, each position associated with the cooperating ratchet interfaces 30a and 30b holds a specific, i.e., constant, strain energy in the shaft members 12a and 12b which, in turn, transmits a specific closing force to the jaw members 110 and 120. It is envisioned that the ratchet 30 may include graduations or other visual markings which enable the user to easily and quickly ascertain and control the amount of closure force desired between the jaw members. A design without a ratchet system or similar system would require the user to hold the jaw members 110 and 120 together by applying constant force to the handles 17a and 17b which may yield inconsistent results.

As best illustrated in FIG. 1, one of the shafts, e.g., 12b, includes a proximal shaft connector 19 which is designed to connect the forceps 10 to a source of electrosurgical energy such as an electrosurgical generator (not shown). More particularly, proximal shaft connector 19 is formed by a cover 19a and a flange 19b which extends proximally from shaft 12b. Preferably, cover 19a and flange 19b mechanically cooperate to secure an electrosurgical cable 210 to the forceps 10 such that the user may selectively apply electrosurgical energy as needed.

The proximal end of the cable 210 includes a plug 200 having a pair of prongs 202a and 202b which are dimensioned to electrically and mechanically engage the electrosurgical energy generator. As explained in more detail below with respect to FIG. 8, the distal end of the cable 210 is secured to the proximal shaft connector 19 of shaft 12b by a plurality of finger-like clamping members 77a and 77b and a cable crimp having opposing fingers 76a and 76b. The interior of cable 210 houses a pair of leads 210a and 210b which conduct the different electrical potentials from the electrosurgical generator to the jaw members 110 and 120 as explained in greater detail below.

As best seen in FIGS. 2-4B, the two opposing jaw members 110 and 120 of the end effector assembly 100 are pivotable about pin 150 from the open position to the closed position for grasping tissue 400 therebetween. Jaw members 110 and 120 are generally symmetrical and include similar component features which cooperate to permit facile rotation about pivot pin 150 to effect the grasping and sealing of tissue 400. As a result and unless otherwise noted, jaw member 110 and the operative features associated therewith will initially be described herein in detail and the similar component features with respect to jaw member 120 will be briefly summarized thereafter.

Figure 4A:
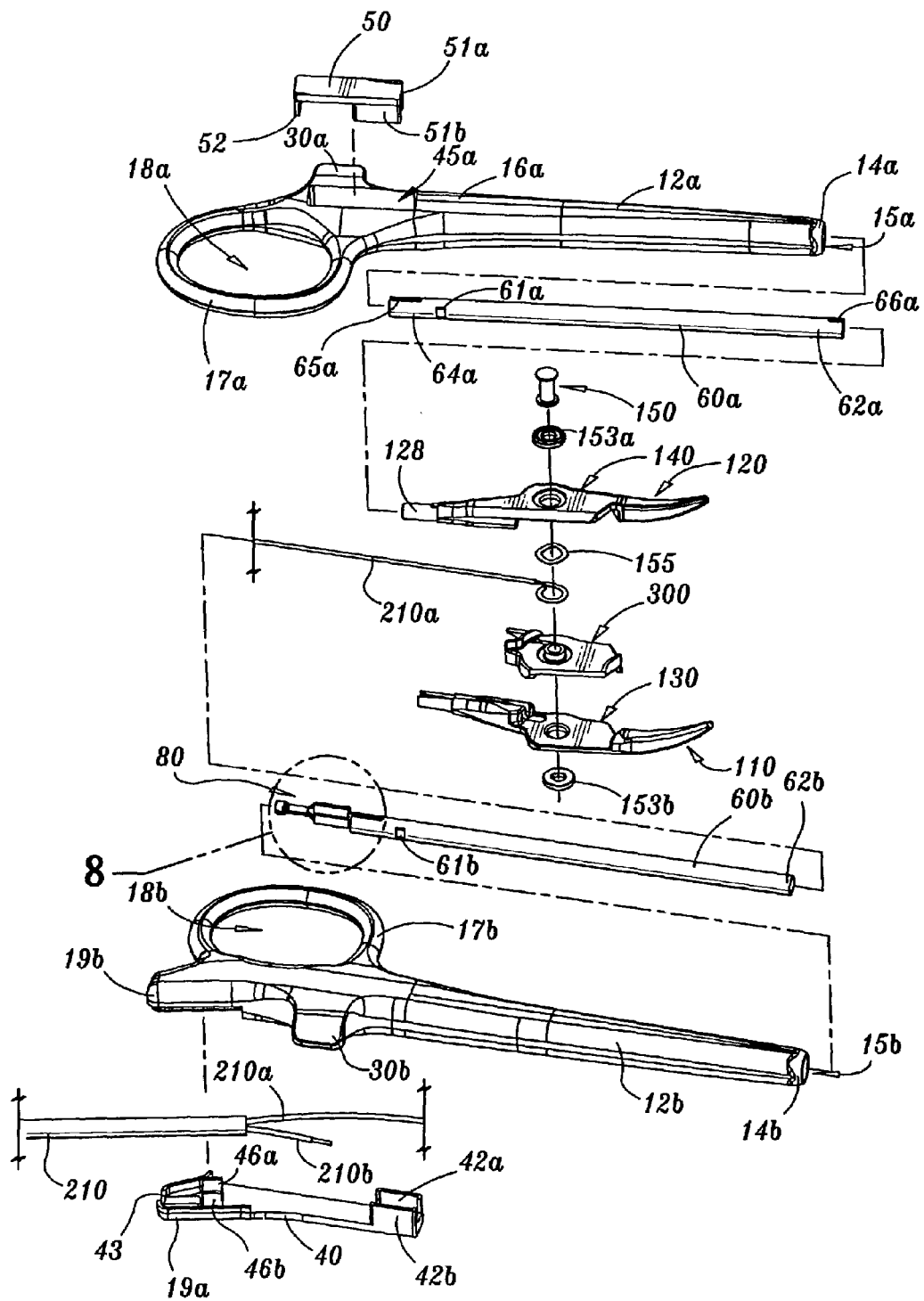
FIG. 4A is an exploded view of the forceps according to the present disclosure.
Figure 4B:
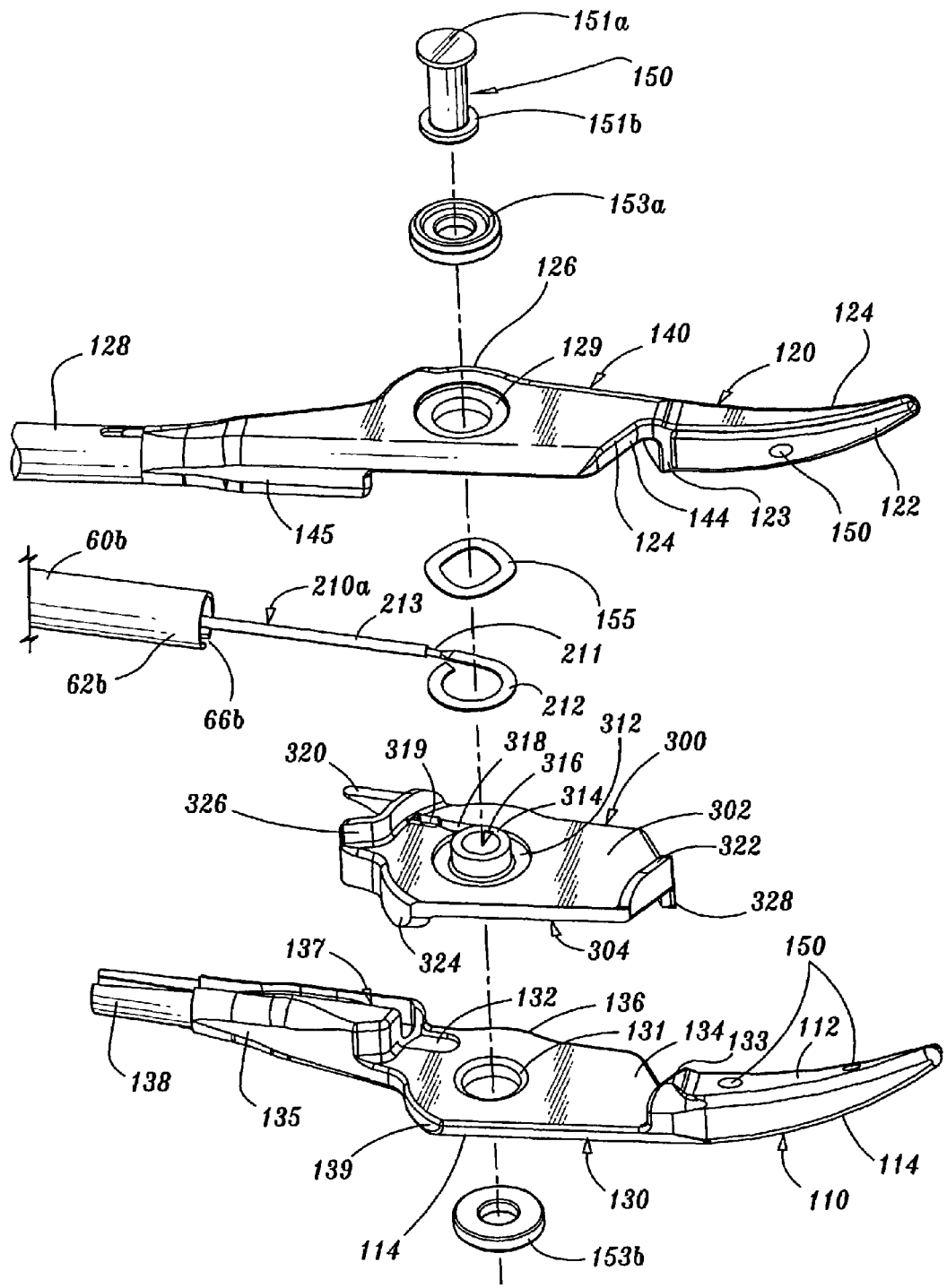
FIG. 4B is an enlarged, exploded view of the end effector assembly of FIG. 4A showing the electrical connection of a distal electrical connector for supplying electrical energy to the end effector assembly.
Figure 5:
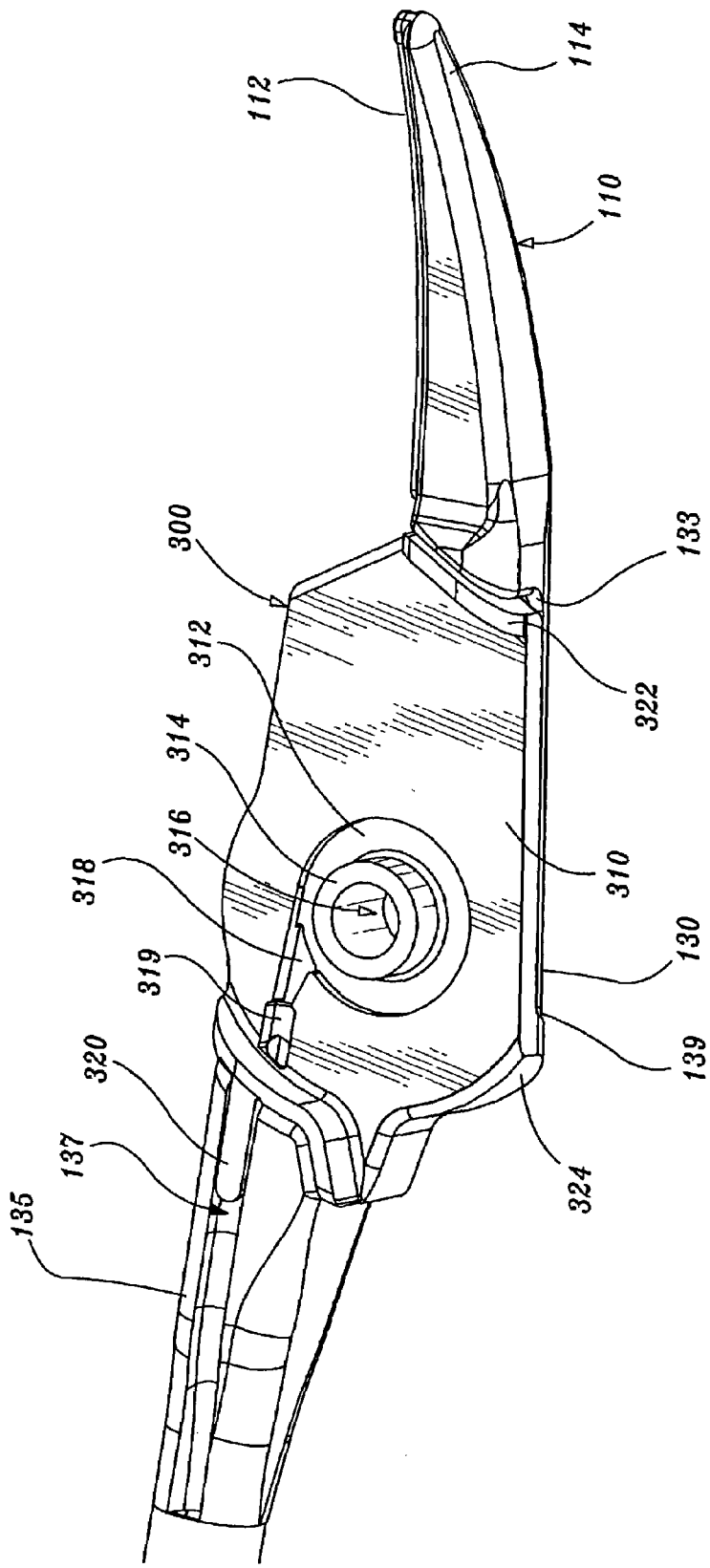
FIG. 5 is an enlarged, top perspective view of a lower jaw member of forceps with the distal connector seated thereon.
Figure 5:
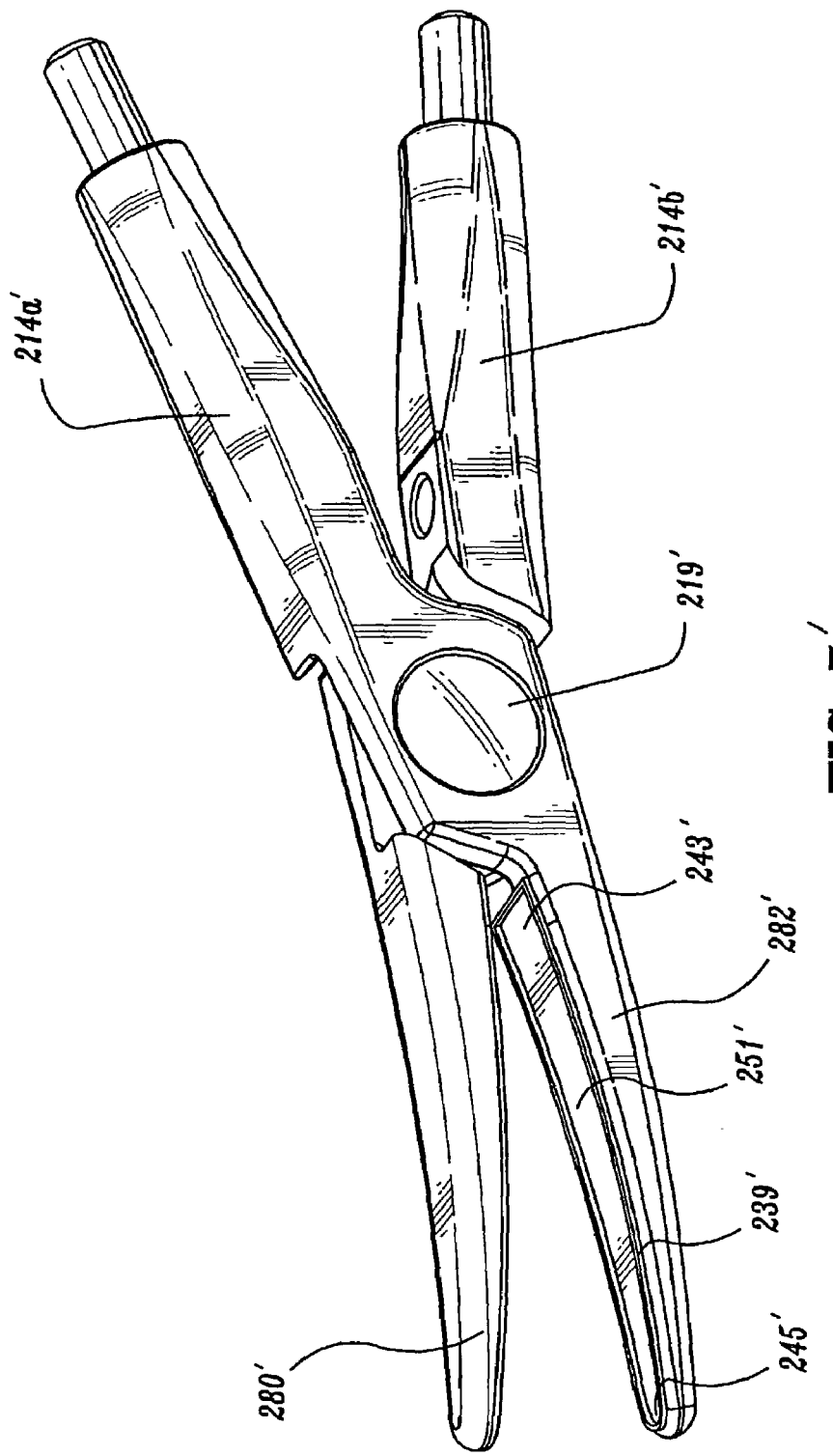

Jaw member 110 includes an insulated outer housing 114 which is dimensioned to mechanically engage an electrically conductive sealing surface 112 and a proximally extending flange 130 which is dimensioned to seat a distal connector 300 which is described in more detail below with respect to FIGS. 4A, 4B and 5. Preferably, outer insulative housing 114 extends along the entire length of jaw member 110 to reduce alternate or stray current paths during sealing and/or incidental burning of tissue 400. The inner facing surface of flange 130 includes an electrically conductive plate 134

(FIG. 4B) which conducts electrosurgical energy to the electrically conductive sealing surface 112 upon activation.

Likewise, jaw member 120 include similar elements which include: an outer housing 124 which engages an electrically conductive sealing surface 122; a proximally extending flange 140 which seats the opposite face of the distal connector 300; an electrically conductive plate 144 which conducts electrosurgical energy to the electrically conductive sealing surface 122 upon activation.

It is envisioned that one of the jaw members, e.g., 110, includes at least one stop member 150 disposed on the inner facing surface of the electrically conductive sealing surface 112 (and/or 122). Alternatively or in addition, the stop member 150 may be positioned adjacent to the electrically conductive sealing surfaces 112, 122 or proximate the pivot pin 151. The stop member(s) is preferably designed to facilitate gripping and manipulation of tissue 400 and to define a gap "G" (FIG. 6) between opposing jaw members 110 and 120 during sealing. Preferably the separation distance during sealing or the gap distance "G" is within the range of about 0.001 inches (~0.03 millimeters) to about 0.006 inches (~0.016 millimeters).

A detailed discussion of these and other envisioned stop members 150 as well as various manufacturing and assembling processes for attaching, disposing, depositing and/or affixing the stop members 150 to the electrically conductive sealing surfaces 112, 122 are described in commonly-assigned, co-pending PCT Application Ser. No. PCT/US01/11222 entitled "BIPOLAR ELECTROSURGICAL FORCEPS WITH NON-CONDUCTIVE STOP MEMBERS" which is hereby incorporated by reference in its entirety herein. For the purposes of this disclosure at least the following text from PCT/US01/11222 is included herein. Corresponding reference numeral to the present disclosure are enclosed between parentheses "( )" for the purposes of clarity. In addition, FIGS. 2, 4, 15B and 16A-16G from the above disclosure are incorporated herein and renumbered as FIGS. 2', 4', 5' and 6A'-6G' for the purposes of clarity. The reference numerals associated with these figures also include a prime "'" designation for the purposes of clarity, e.g., 80', 82', etc.

As mentioned above, two mechanical factors play an important role in determining the resulting thickness of the sealed tissue and effectiveness of the seal, i.e., the pressure applied between opposing jaw members 80' and 82' (110 and 120) and the gap between the opposing jaw members 80' and 82' (110 and 120) during the sealing process. However, thickness of the resulting tissue seal cannot be adequately controlled by force alone. In other words, too much force and the two jaw members 80' and 82' (110 and 120) would touch and possibly short resulting in little energy traveling through the tissue thus resulting in a bad seal. Too little force and the seal would be too thick.

Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Figure 2:
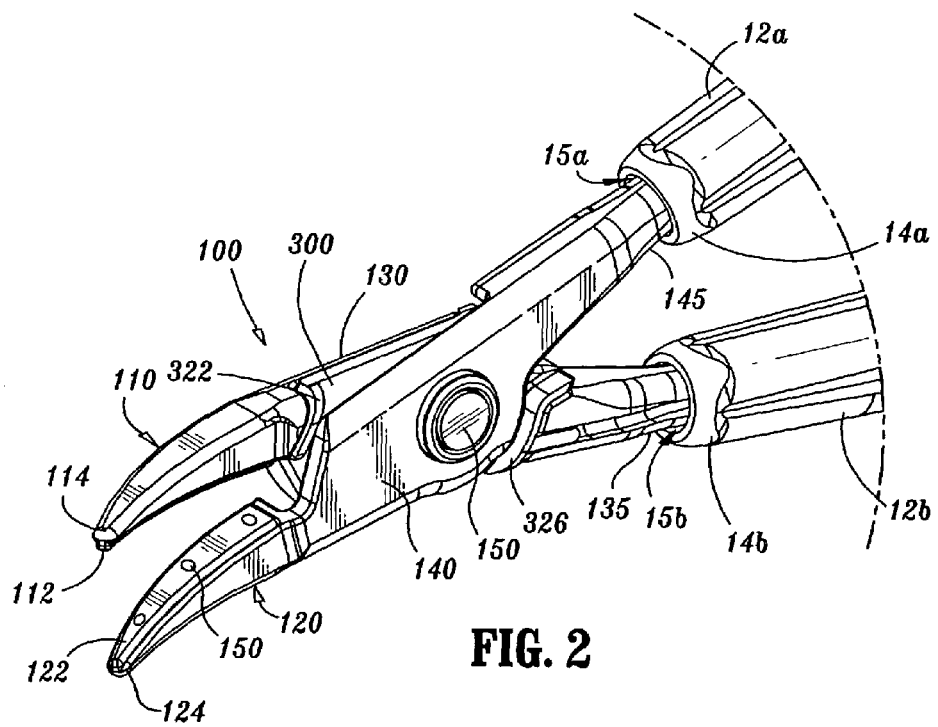
FIG. 2 is an enlarged, perspective view of an end effector assembly of the forceps of FIG. 1 shown in open configuration.
Figure 3:
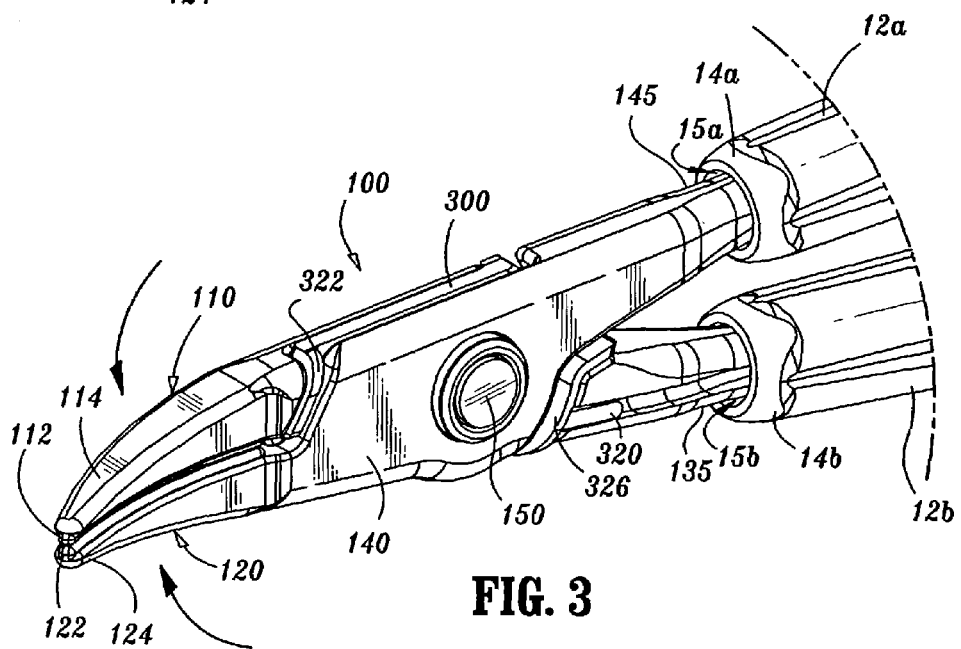
FIG. 3 is an enlarged, perspective view of the end effector assembly of the forceps of FIG. 1 shown in closed configuration.

Preferably, the seal surfaces or tissue contacting surfaces 151', 251' (112, 122) (See renumber FIGS. 5' and 6A'-6G') of the jaw members 80' and 82' (110 and 120) are relatively flat to avoid current concentrations at sharp edges and to avoid arcing between high points. In addition and due to the reaction force of the tissue 150 when engaged, jaw members 80' and 82' (110 and 120) are preferably manufactured to resist bending. For example and as best seen in FIGS. 2' and 6A'-6G', the jaw members 80' and 82' (110 and 120) are preferably tapered along width "W" which is advantageous for two reasons: 1) the taper will apply constant pressure for a constant tissue thickness at parallel; 2) the thicker proximal portion of the jaw members 80' and 82' (110 and 120) will resist bending due to the reaction force of the tissue 150.

Figure 4:
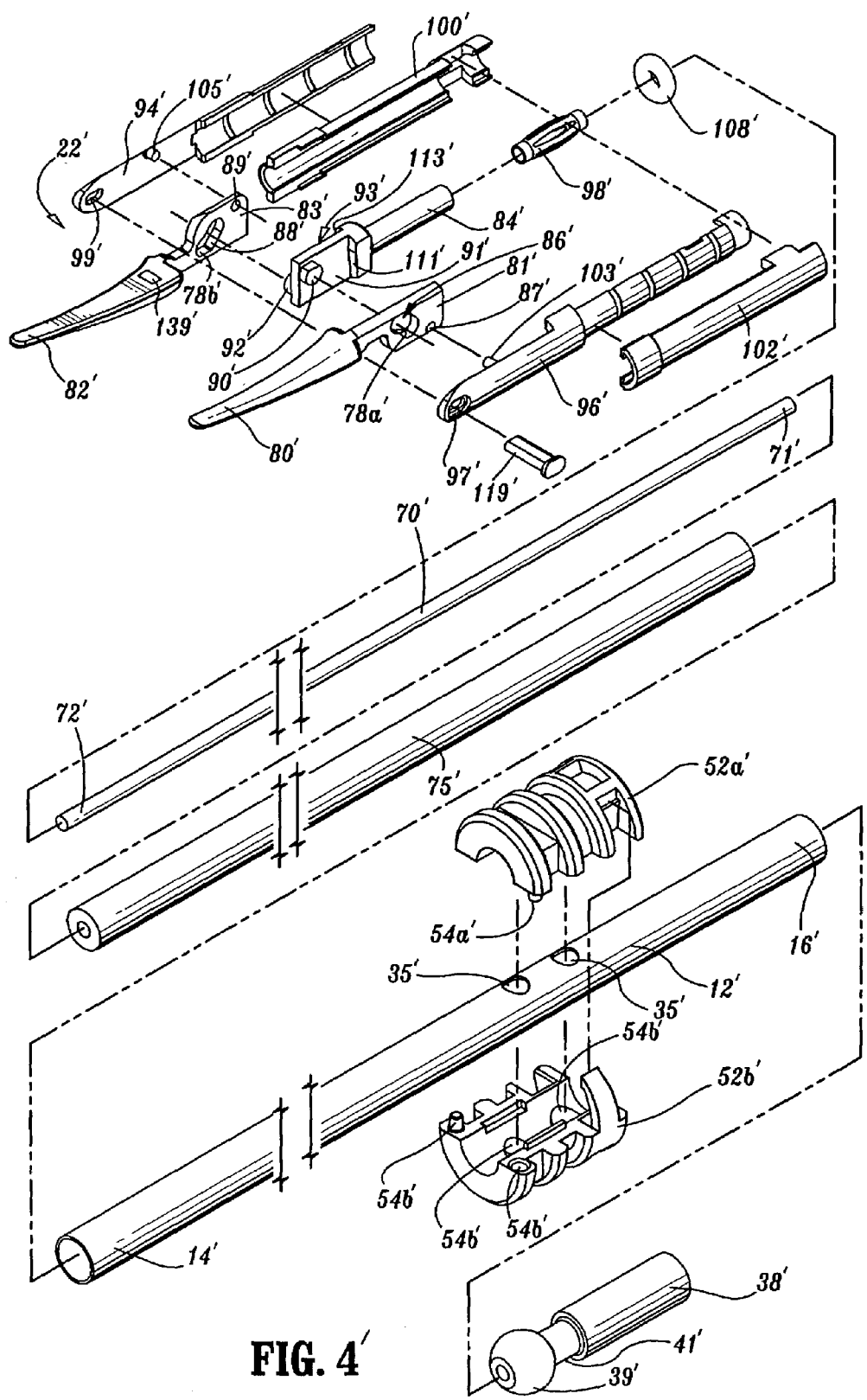
FIG. 4' is an enlarged, exploded view of the end effector assembly of a bipolar instrument incorporated by reference from a prior disclosure.

As best seen in FIG. 4', in order to achieve a desired gap range (e.g., about 0.001 to about 0.005 inches and preferably about 0.002 inches to about 0.003 inches) and apply a desired force to seal the tissue, at least one jaw member 80' and/or 82' (110 and 120) includes a stop member 139' (150) which limits the movement of the two opposing jaw members 80' and 82' (110 and 120) relative to one another. Preferably, stop member 139' (150) extends from the sealing surface or tissue contacting surface 151' (112 or 122) a predetermined distance according to the specific material properties (e.g., compressive strength, thermal expansion, etc.) to yield a consistent and accurate gap distance during sealing.

As explained above, in some cases it may be preferable to dimension stake 119' such that it acts like a stop member and/or an additional stop member and also controls/limits the movement of the two opposing jaw members 80' and 82' (110 and 120) relative to one another. Preferably, stop member 139' (150) and/or stake 119' is made from an insulative material, e.g., parylene, nylon and/or ceramic and is dimensioned to limit opposing movement of the jaw members 80' and 82' (110 and 120) to within the above gap range.

FIG. 4A shows an exploded view of the various components of the forceps 10 and the inter-operative relationships among the same. More particularly and in addition to the components described above with respect to FIGS. 1-3 above, shaft 12a is preferably hollow to define a longitudinal channel 15a disposed therethrough which is dimensioned to receive a tube 60a therein. Tube 60a includes a proximal end 64a, a distal end 62a and at least one mechanical interface 61a disposed therebetween. Shaft 12a also includes a cover plate 50 which is designed for snap-fit engagement within an aperture/cavity 45a defined through the outer surface of shaft 12a. Cover plate 50 includes a series of opposing flanges 51a and 51b which extend therefrom which are dimensioned to secure the tube 60a within shaft 12a as described below. A second flange 52 secures the cover plate 50 to the shaft 12a.

During assembly, the proximal end 64a of tube 60a is slideable incorporated within channel 15a such that mechanical interface 61a is poised for engagement with cover plate 50. Cover plate 50 is then snapped into cavity 45a such that flanges 51a and 51b secure tube 60a within shaft 12a. It is envisioned that the cavity 45a of shaft 12a may include at least one detent (not shown) which engages mechanical interface 61a disposed along the outer surface of tube 60a to limit/prevent rotation of the tube 60a relative to the shaft 12a. This cooperative relationship is shown by way of example with respect to detents 75a and 75b and interfaces (e.g., notches) 61b of shaft 12b in FIG. 8. In this instance, flanges 51a and 51b (much like flanges 42a and 42b of cover plate 40 in FIG. 8) hold the detents 75a and 75b in FIG. 8) in secure engagement within the notch(es) 61a to prevent rotational and/or longitudinal movement of the tube 60a within the channel 15a.

Preferably, the proximal-most end of tube 60a includes a slit-like interface 65a which mechanically engages a corresponding tongue 88a extending from the inner surface of shaft 12a within cavity 45a. It is envisioned that tongue 88a also prevents rotational movement of the tube 60a within the shaft 12a. Alternatively, slit 65a may be formed to allow radial contraction and expansion of the tube 60a to promote friction-fit engagement between the tube 60a and the shaft 12a. Other interfaces are also envisioned which will facilitate engagement of the shaft 12a and the tube 60a, e.g., snap-fit, spring-lock, locking tabs, screw-like interface, tongue and groove, etc.

The distal end 62a of tube 60a is preferably dimensioned to engage jaw member 120, i.e., the distal end 62a includes a slit-like interface 66a which promotes simple, secure friction-fit engagement of the tube 60a with the jaw member 120. More particularly and as mentioned above, jaw member 120 includes a proximally extending flange 130 having a sleeve 128 extending proximally therefrom which is dimensioned such that, upon insertion of the sleeve 128 within distal end 62a, slit-like interface 66a expands radially outwardly and securely locks the jaw member 120 to tube 60a. Again, other methods of attachment are also envisioned which would serve the same purpose, e.g., snap-locks, locking tabs, spring-locks, screw-like interface, tongue and groove, etc.

Figures 7, 8:
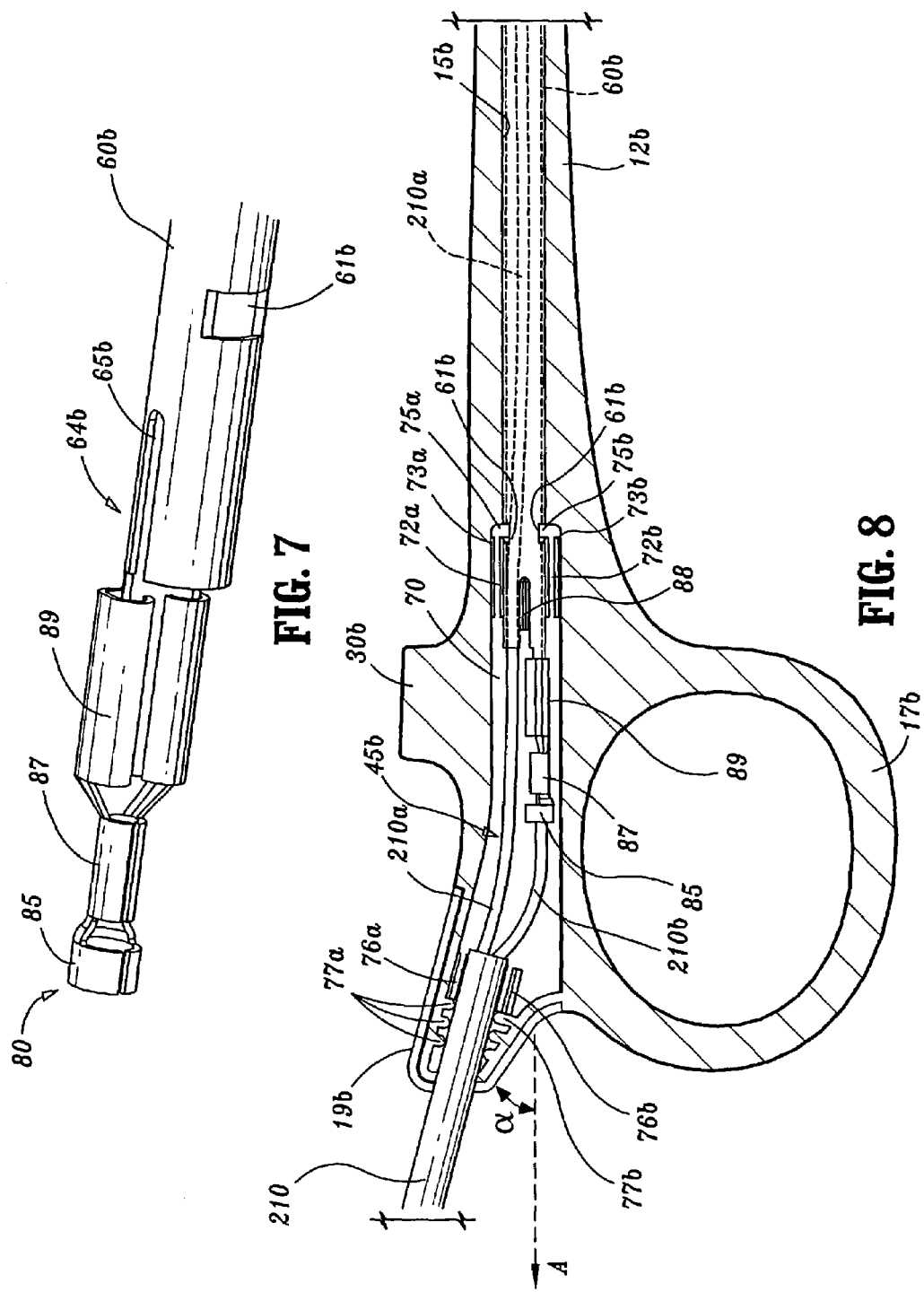
FIG. 7 is a enlarged view of the indicated area of detail in FIG. 4A showing a proximal electrical interface/connector for supplying electrical energy to the end effector assembly.
FIG. 8 is a cross section of the forceps of FIG. 6 showing the electrical feed path of a first lead having a first electrical potential and showing the electrical connection of the proximal electrical interface of FIG. 7 with a second lead having a second electrical potential.

As can be appreciated by the present disclosure, the arrangement of shaft 12b is slightly different from shaft 12a as shown best in FIGS. 4B, 7 and 8. More particularly, shaft 12b is also hollow to define a channel 15b therethrough and is dimensioned to receive a tube 60b therein. Tube 60b includes a proximal end 64b and a distal end 62b which attach in a generally similar fashion as their counterpart components with respect to shaft 12a. For example, the proximal end 64b of tube 60b is slideable incorporated within channel 15b such that a mechanical interface 61b disposed on the outer surface of tube 60b is poised for engagement with a cover plate 40 (FIGS. 4A and 8).

Preferably and since the forceps 10 is uniquely designed to incorporate all of the electrical interfaces and connections within and along a single shaft, e.g., 12b, shaft 12b includes a slightly larger cavity 45b defined therein for housing and securing the various electrical connections associated with the forceps 10 as described below. For example, cover plate 40 is dimensioned slightly differently than cover plate 50 mostly due to the spatial considerations which must be taken into account for incorporation of the various internally disposed electrical connections. However, cover plate 40 does snap atop shaft 12b such that a pair of flanges 42a and 42b secure tube 60b within shaft 12b in a similar manner as described above. For example, FIG. 8 shows a pair of detents 75a and 75b disposed within the cavity 45b of shaft 12b which engage a corresponding number of mechanical interfaces 61b disposed along the outer surface of tube 60b to limit/prevent rotation of the tube 60b relative to the shaft 12b. When assembled, each flange 42a and 42b is pushed into a corresponding groove 73a and 73b, respectively, which effectively maintain/hold the detents 75a and 75b in secure engagement within the notches 61b to prevent rotational and/or longitudinal movement of the tube 60b within the channel 15b.

End 64b of tube 60b also includes a slit-like interface 65b which mechanically engages a corresponding tongue 88b extending from the inner surface of shaft 12b within cavity 45b. It is envisioned that tongue 88a also prevents rotational movement of the tube 60b within the shaft 12b. Alternatively, slit 65b may be formed to allow radial contraction and expansion of the tube 60b to promote friction-fit engagement between the tube 60b and the shaft 12b.

Unlike tube 60a, tube 60b is designed as an electrical conduit for transmitting electrosurgical energy to jaw member 110 which is explained in more detail below with respect to FIGS. 7 and 8. The distal end 62b of tube 60b is preferably dimensioned to engage jaw member 110, i.e., the distal end 62b includes a slit-like interface 66b which promotes simple, secure friction-fit engagement of the tube 60b with the jaw member 110. This is best illustrated in FIG. 4B which shows proximally extending flange 130 of jaw member 110 having a terminal sleeve 138 which extends therefrom. Terminal sleeve 138 is dimensioned such that, upon insertion of the terminal sleeve 138 within distal end 62b, slit-like interface 66b expands radially outwardly and securely locks the jaw member 110 to tube 60b.

As can be appreciated, terminal end 138 is at least partially made from an electrically conductive material such that an electrosurgical potential is effectively conducted from the tube 60b, through the terminal sleeve 138, across plate 134 and to the electrically conductive sealing plate 112 upon activation. As mentioned above, the outer insulative housing 114 of jaw member 110 effectively eliminates stray electrical currents and incidental burning of tissue across the intended electrical path.

As best shown in FIG. 4B, jaw member 110 includes a raceway 135 extending proximally from the flange 130 which includes terminal sleeve 138 at the proximal-most end thereof. The terminal sleeve 138 connects to the conductive tube 60b disposed within shaft 12b as described above. Raceway 135 serves two purposes: 1) to provide electrical continuity from the terminal sleeve 138, through the electrically conductive plate 134 and to the electrically conductive sealing surface 112; and 2) to provide a channel for guiding lead 210a to the distal connector 300 as described below.

Insulated outer housing 114 is dimensioned to securely engage the electrically conductive sealing surface 112. It is envisioned that this may be accomplished by stamping, by overmolding, by overmolding a stamped electrically conductive sealing plate and/or by overmolding a metal injection molded seal plate. All of these manufacturing techniques produce an electrode having an electrically conductive surface 112 which is substantially surrounded by an insulated outer housing 114.

It is envisioned that the jaw member may also include a second insulator (not shown) disposed between the electrically conductive sealing surface 112 and the outer insulative housing 114. The insulated outer housing 114 and the electrically conductive sealing surface 112 (and the other insulator if utilized) are preferably dimensioned to limit and/or reduce many of the known undesirable effects related to tissue sealing, e.g., flashover, thermal spread and stray current dissipation.

It is also envisioned that the electrically conductive sealing surface 112 may include a pinch trim (not shown) which facilitates secure engagement of the electrically conductive surface 112 to the insulated outer housing 114 and also simplifies the overall manufacturing process. It is also contemplated that the electrically conductive sealing surface 112 may include an outer peripheral edge which has a radius and the insulated outer housing 114 meets the electrically conductive sealing surface 112 along an adjoining edge which is generally tangential to the radius and/or meets along the radius. Preferably, at the interface, the electrically conductive surface 112 is raised relative to the insulated outer housing 114. These and other envisioned embodiments are discussed in concurrently-filed, co-pending, commonly assigned Application Ser. No. PCT/US01/11412 entitled "ELECTROSURGICAL INSTRUMENT WHICH REDUCES COLLATERAL DAMAGE TO ADJACENT TISSUE" by Johnson et al. and concurrently-filed, co-pending, commonly assigned Application Ser. No. PCT/US01/11411 entitled "ELECTROSURGICAL INSTRUMENT WHICH IS DESIGNED TO REDUCE THE INCIDENCE OF FLASHOVER" by Johnson et al.

As best illustrated in the exploded view of FIG. 4B, the inner periphery of tube 60b is preferably dimensioned to house lead 210a therethrough such that a different electrically potential can be effectively transmitted to jaw member 120. More particularly and as mentioned above, cable 210 houses two leads 210a and 210b having different electrical potentials. The first lead 210a is disposed through tube 60b and conducts the first electrical potential to jaw member 120 as described in more detail below. The second lead 210b is electrically interfaced with tube 60b at a proximal connector 80 (FIG. 7) which includes a series of electrical crimps 85, 87 and 89 for securing lead 210b to tube 60b. As a result, tube 60b carries the second electrical potential therethrough for ultimate connection to jaw member 110 as described above.

Lead 210a preferably includes an insulative coating 213 which surrounds an inner core or electrical conductor 211 (e.g., wire) disposed therein to insulate the electrical conductor 211 from the tube 60b during activation. It is envisioned that the wire 211 may be made from a solid or multi-strand electrically conductive material, e.g., copper/aluminum, which is surrounded by an insulative, non-conductive coating 213, e.g., plastic.

The wire 211 includes a terminal end 212 which is dimensioned to electrically interface with jaw member 120. Preferably, the terminal end 212 is "flatformed" in a generally arcuate shape to encircle a corresponding boss 314 which extends upwardly from the distal connector 300 towards jaw member 120 as described below. It is envisioned that the distal connector 300 performs at least two functions: 1) to insulate jaw member 110 from jaw member 120; and 2) to provide a running electrical connection for lead 210a to jaw member 120.

More particularly, the distal connector 300 is generally shaped to match the overall profile of the electrically conductive face plates 134 and 144 of jaw members 110 and 120, respectively, such that, upon assembly, outer facing surfaces 302 and 304 of the distal connector 300 abut against the corresponding plates 134 and 144 of jaw member 110 and 120, respectively. It is envisioned that the outer facing surface 302 of the distal connector 300 acts as a runway surface which facilitates pivotable motion of jaw member 120 about pivot pin 151 relative to jaw member 110. Preferably, the distal connector 300 is made form an insulative substrate such as plastic or some other non-conductive material.

The distal connector includes a series of flanges 322 and 326 which extend towards jaw member 120 and a second series of flanges 324 and 328 which extend towards jaw member 110. It is envisioned that these flanges 322, 324, 326 and 328 insulate the other operative components of the forceps 10 and the patient from stray electrical currents emanating from the electrically conductive plates 134 and 144 during activation. Flanges 322 and 328 may also be dimensioned to limit/restrict the expansion of tissue 400 beyond the sealing surfaces 112 and 122 during activation. Flanges 326 and 324 are preferably dimensioned to insulate the forceps during all angles of operation, i.e., pivoting of the jaw members 110 and 120.

As mentioned above, the distal connector 300 includes a boss 314 which extends towards jaw member 120 which is dimensioned to secure the terminal end 212 of lead 210a. Preferably, the boss is designed to electrically insulate the terminal end of the lead from the pivot. The boss 314 preferably defines an aperture 316 therethrough for receiving the pivot pin 151 and to allow pivotable motion of jaw member 120 about the pivot 151 and the boss 314 relative to jaw member 110.

A continuous series of recesses 312, 318 and 319 are formed around and proximate boss 314 to seat the flat-formed terminal end 212, the wire 211 and the insulated portion of the lead 210a, respectively. This also secures lead 210a to the distal connector and limits movement of the same (210a). In some cases it may be preferable to include a dollop of silicone or other non-conductive material at the junction between the wire and the terminal end 212 as an added and/or alternative insulating safeguard. It is also envisioned that flange 326 may include a notch (not shown) disposed therethrough which facilitates assembly of the lead 210a atop the distal connector 300. As can be appreciated, this eliminates the step of forming the arcuately-shaped terminal end 212 after insertion through channel 318. As mentioned above, a dollop of silicone or the like may be added atop/within the notch for insulation purposes after the terminal end 212 is seated within the distal connector 300.

The proximal-most portion of distal connector 300 includes a finger 320 which is dimensioned to seat within a channel 137 formed within the raceway 135 such that the distal connector 300 moves in connection with jaw member 110 during pivoting. Channel 135 may be formed during a molding process, subsequently bored after the raceway 135 is formed or by any other known method of formation. The uppermost edge of boss 314 is preferably dimensioned to seat within a corresponding recess (not shown) formed within plate 144. Likewise and although not shown, it is envisioned that the opposite end of boss 314 extends towards plate 134 and seats within a recess 131 formed within plate 134. It is envisioned that recess 131 promotes engagement of the distal connector 300 with the jaw member 110.

The distal connector 300 also includes a spring washer or wave washer 155 which is preferably dimensioned to encircle the boss 314 atop terminal end 212. Upon assembly, the washer 212 is sandwiched/wedged between the terminal end 212 and the conductive plate 144 of jaw member 120. It is envisioned that the washer 155 enhances the connection between the terminal end and the plate 144. More particularly, the washer 155 is preferably shaped such that the washer 155 provides a self-cleaning, running electrical contact between the terminal end 212 and the jaw member 120. It is contemplated that the washer 155 "self-cleans" due to the frictional contact and relative movement of the washer 155 with respect to the terminal end 212 during pivoting of the jaw members 110 and 120. The self-cleaning action can be attributed to the washer 155 rubbing, scoring and/or digging against the terminal end 212 and/or the plate 144 during pivoting of the jaw members 110 and 120.

Alternatively, it is envisioned that the present disclosure may include a dome-like switch or k-pin which provides electrical contact with the flat-formed terminal end 212. Moreover, it is also contemplated that the proximally extending flange may include a conductive tab (not shown) which depends therefrom to provide electrical continuity between the terminal end 212 and the jaw member 120. The terminal end 212 may also be dimensioned as a non-conductive loop which encircles the corresponding boss 314. The conductive surface may be vapor deposited (plasma vapor deposition (PVD)) or thermally sprayed on the nonconductive surface as part of an additional manufacturing step.

One embodiment of the present disclosure may include a PCB or flex circuit (not shown) which affixes to lead 210a at a distal end thereof. The PCB provides electrical continuity to jaw member 120 and may be configured to measure other electrical or mechanical parameters (e.g., smart circuit) across the jaw members prior to and or during activation. For example, the PCB circuit may provide information relating to the gap distance (i.e. proximity detector) between the two jaw members 110 and 120, the sealing pressure between the jaw members 110 and 120 prior to and during activation, load (i.e., strain gauge), the tissue thickness prior to or during activation, the impedance across the tissue during activation, the temperature during activation, the rate of tissue expansion during activation and sealing. It is envisioned that the PCB circuit may be designed to provide electrical feedback back to the generator relating to one or more of the above parameters either on a continuous basis or upon inquiry from the generator. For example, a PCB circuit may be employed to control the power, current and/or type of current waveform from the generator to the jaw members to facilitate the desired surgical effect (i.e., cutting, coagulation, blend, sealing) and/or to reduce collateral damage to surrounding tissue during activation, e.g., thermal spread, tissue vaporization and/or steam from the treatment site. Examples of a various control circuits, generators and algorithms which may be utilized are disclosed in U.S. Pat. No. 6,228,080 and U.S. application Ser. No. 10/073,761 the entire contents of both of which are hereby incorporated by reference herein.

The outer housing of each of the jaw members 110 and 120 preferably includes an additional recess or circular groove 129 which receives a ring-like insulator 153b and 153a, respectively. Insulators 153a and 153b insulate the pivot pin 150 from the jaw members 110 and 120 when the forceps 10 is assembled. Preferably, the pivot pin 150 is peened to secure the jaw members 110 and 120 during assembly and may include outer rims 151a and 151b at least one of which is peened or formed after the jaw members 110 and 120 are assembled about the pivot pin 150 as best shown in FIG. 4B.

Upon activation, the first electrical potential is carried by lead 210a through tube 60b to the terminal end 212. The washer 155 of the distal connector 300 then conducts the first potential to face plate 144 which carries the first potential to sealing plate 122 disposed on the inner facing surface of jaw member 120. The second potential is carried by lead 210b which electrically interfaces with the tube 60b (by way of crimps 85, 87 and 89) to conduct the second potential to terminal sleeve 138 of jaw member 110. The terminal sleeve 138 electrically connects to sealing surface 112 across face plate 134.

FIG. 8 shows the connection of the cable 210 within the cavity 45b of shaft 12b. As mentioned above a series of finger-like elements 77a and 77b and crimps 76a and 76b secure the cable 210 within shaft 12b. Preferably, cable 210 is secured at an angle alpha (α) relative to a longitudinal axis "A" disposed along shaft 12b. It is envisioned that angling the cable 210 in an inward direction, i.e., towards shaft 12a, facilitates handling of the forceps 10 and the cable 210 during surgery, i.e., the angled disposition of the cable 210 as it exits the forceps 10 tends to reduce cable tangling and/or cable interference during handling.

Preferably at least one of the jaw members 110 and 120 includes a skirt-like feature 126 and 136, respectively, which is dimensioned to prevent exposure of the terminal end 212 or wire 211 during all angles of operation, i.e., when the jaw members 110 and 120 are disposed in the first open position, the second closed position and/or during operative movement therebetween.

It is envisioned that by making the forceps 10 disposable, the forceps 10 is less likely to become damaged since it is only intended for a single use and, therefore, does not require cleaning or sterilization. As a result, the functionality and consistency of the vital sealing components, e.g., the conductive surfaces 112 and 122, the stop member(s) 150, and the insulative housings 124 and 114 will assure a uniform and quality seal.

Figure 9A:
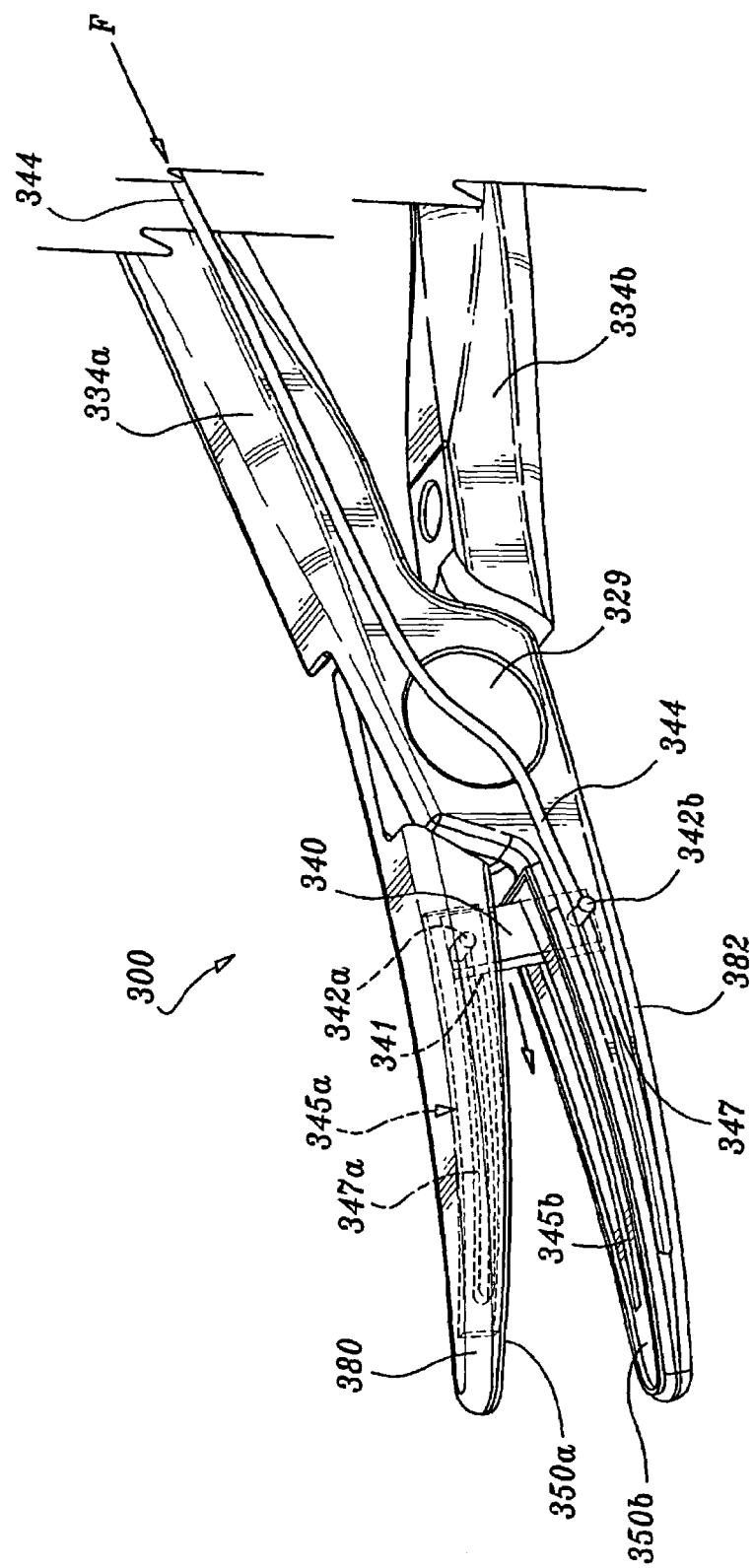
FIG. 9A is a perspective view of an alternate embodiment of the present disclosure showing a selectively advanceable knife assembly disposed between opposing jaw members.
Figure 9B:
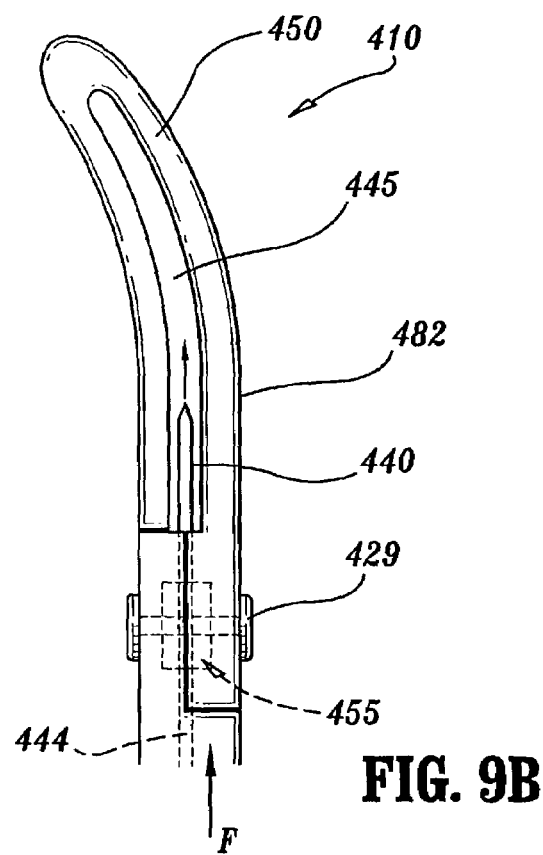
FIG. 9B is a top view of another embodiment of the present disclosure showing the knife assembly disposed through a spacer within the pivot area.
Figure 9C:
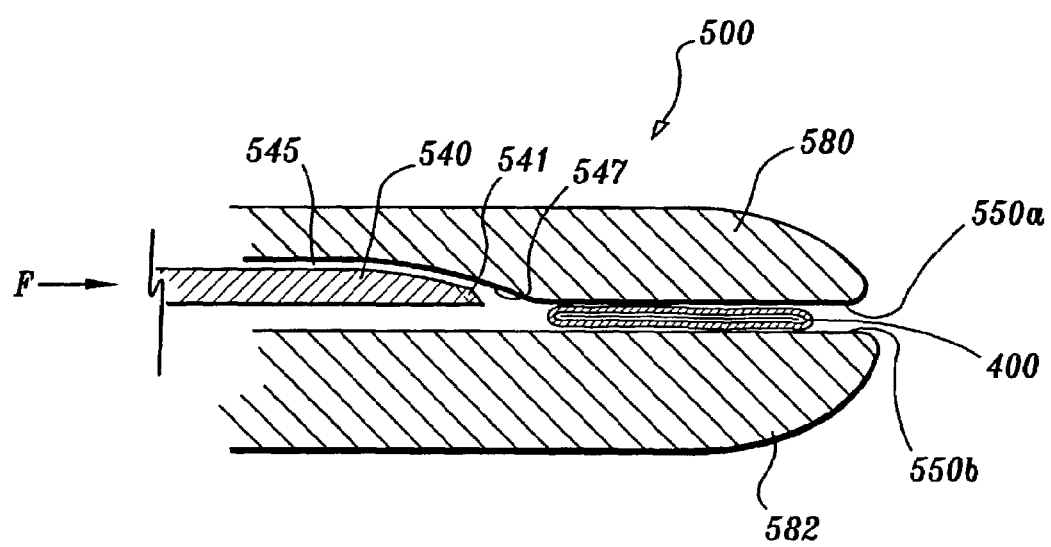
FIG. 9C is a side cross sectional view of another embodiment of the present disclosure showing a knife assembly disposed within a cam-like recess in one of the jaw members.

FIGS. 9A-9C show another embodiment of the present disclosure which employs a selectively advanceable knife assembly which allows the surgeon to separate the tissue 400 once sealed. For example, FIG. 9A shows one embodiment wherein the forceps 300 includes two opposing jaw members 380 and 382 which cooperate to engage tissue 400 therebetween upon rotation of the jaw members 380 and 382 about pivot 329. The surgeon selectively applies a combination of electrosurgical energy and pressure to effective seal the tissue 400 between sealing surfaces 350a and 350b as described in detail in one or more of the above embodiments shown in the previous figures. Each jaw member 380 and 382 also includes a knife channel or slot 345a and 345b, respectively, which extends longitudinally along the respective jaw member between the sealing surfaces 350a and 350b. A knife 340 having a leading cutting edge 341 is housed between the two slots 345a and 345 and is selectively translatable by the surgeon to sever the tissue 400 along the sealing plane. More particularly, a pair of pins 342a and 342b retain the knife within the slots 345a and 345b, respectively, and allow the surgeon to distally reciprocate the knife 340 by remotely actuating a control rod 344 which connects to at least one of the pins, e.g., 342b. Each pin 342a, 342b rides along a guide channel 347a and 347b disposed on the side of each jaw member 380, 382, respectively. Once severed, the surgeon simply retracts the rod 344 proximally to reposition the knife 340 for cutting the next seal. It is envisioned that the knife 340 may be conductive and coupled to the same or different source of electrosurgical energy to facilitate separation of the tissue 400 along the tissue seal. The knife may also be made from a non-conductive material depending upon a particular purpose.

FIG. 9B shows an alternative embodiment of a forceps 410 according to the present disclosure which includes a knife 440 which is translatable through a spacer 455 disposed within the pivot assembly 429. Again the knife 440 is translatable through a slot 445 disposed within each of the jaw members, e.g., 482, to sever tissue 400 along the sealing plane. A control rod 444 allows the surgeon to selectively translate the knife 440 once the tissue 400 is sealed.

FIG. 9C shows another embodiment of a forceps 500 according to the present disclosure wherein one of the jaw members, e.g., 580, houses the knife 540 within a recess 545 therein. Preferably, the recess 545 is disposed at a point which is proximal to the tissue sealing surfaces 550a and 550b. The recess 545 includes a cammed surface 547 at the distal end thereof. During the initial sealing process, the knife 540 is maintained in a first position wherein the knife 540 is wholly retained within the recess 545 to allow the surgeon to grasp and manipulate the tissue 400 as need to effect a good seal. Once sealed, the surgeon remotely advances the knife 540 distally against the cammed surface 547 which causes the leading edge 541 of the knife 540 to deflect into and through the tissue 400. It is envisioned that the knife 540 may be spring-biased such that once the tissue 400 is severed the knife 540 automatically returns to the first position within the recess 545.

Figure 9D:
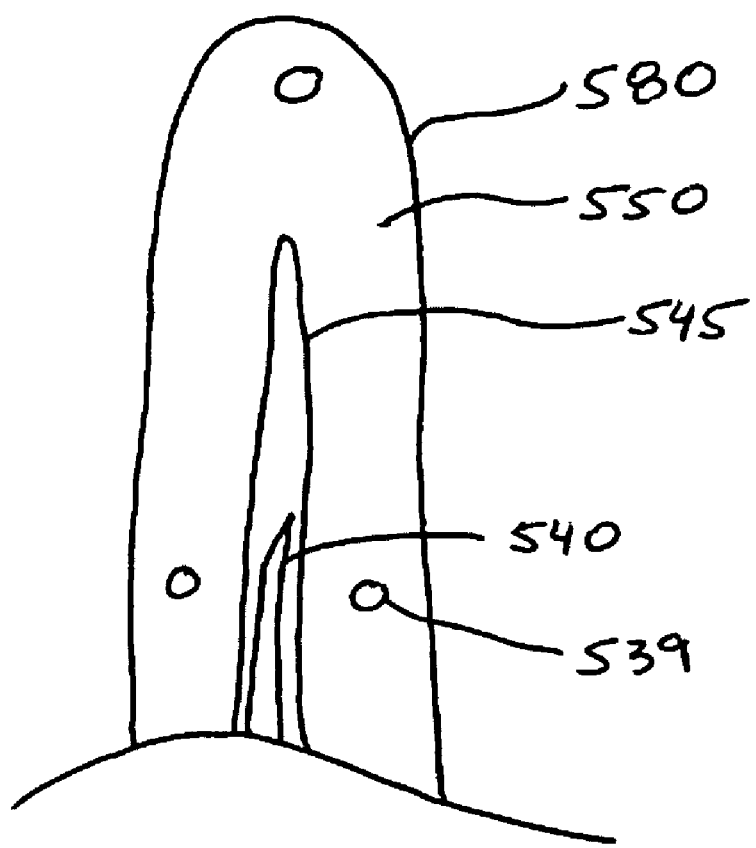
FIG. 9D is a top view of another embodiment of the present disclosure showing a jaw member housing a knife in a knife channel and including at least one non-conductive stop member.

FIG. 9D shows yet another embodiment of a forceps 500 according to the present disclosure wherein at least one of the jaw members, e.g. 580, houses the knife 540 which is selectively reciprocal within knife channel 545 and further includes at least one non-conductive stop member 539 positioned on at least one tissue sealing surface 550. Knife channel 545 allows the knife 540 to be selectively advanced through sealed tissue 400 held between the jaw members.

Figure 10A:
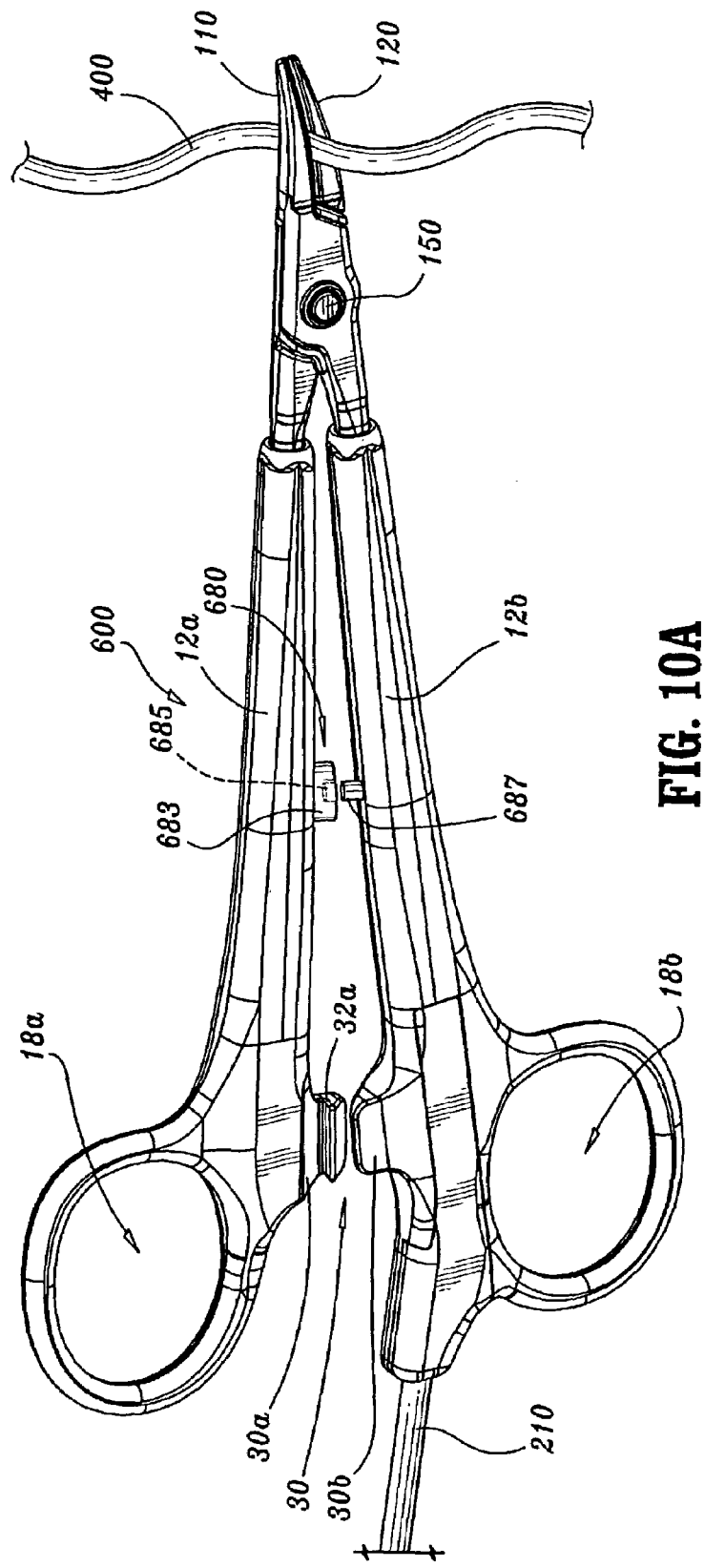
FIG. 10A is a side perspective view of another embodiment according to the present disclosure showing a pin-like electromechanical contact which provides electrical continuity across the jaw members when the jaw members are closed.

FIG. 10A shows yet another alternate embodiment of a forceps 600 according to the present disclosure which includes a gap electrical connection 680 disposed between the two shafts 12*a* and 12*b* of the forceps 600. More particularly, the gap connection 680 includes two opposing electromechanical interfaces 683 and 687 on each of the shafts 12*a* and 12*b*, respectively, which align for electrical communication therebetween, e.g., pin 687 engages a corresponding slot 685 disposed in connection 683. As can be appreciated, the gap connection 680 provides an additional safety feature to the forceps 600. For example, in an open configuration, the surgeon is free to approximate, manipulate and grasp tissue 400 as needed without electrically continuity being provided to the jaw members, i.e., the jaw members 110 and 120 cannot be electrosurgically energized in an open configuration. Once the jaw members 110 and 120 are closed about the tissue 400, the two opposing electromechanical interfaces 683 and 687 mechanical and electrically engage to complete the electrosurgical circuit and allow electrosurgical energy to flow through the tissue 400.

It is envisioned that the pin 687 and slot 685 can be dimensioned such that the electrical circuit is completed only when the ratchet mechanism is engaged or based upon a predetermined position of the inter-engaging ratchet interfaces 30*a* and 30*b*. For example, if the opposing ratchet interfaces 30*a* and 30*b* include a plurality of discrete positions corresponding to incremental closure forces about the tissue 400, the electromechanical interfaces 683 and 687 of the gap connection 680 may be dimensioned such that only the latter positions complete the electrical circuit. As can be appreciated, this allows the surgeon to freely utilize the forceps 600 in a conventional manner to manipulate, grasp and hold the tissue 400 without the fear of inadvertently electrifying the tissue 400. When sealing is desired, the surgeon simply further engages the ratchet 30 to a predetermined ratchet position which provides electrical continuity to the jaw members 110 and 120.

Moreover, by utilizing a gap connection 680, both electrical potentials may be bundled into a single cable 210 attachable to one of the two shafts, e.g., 12*b*, which reduces inadvertent cable tangling during use. The second electrical potential is carried across the gap connection 680 to the respective jaw member, e.g., jaw member 110, 110 when the gap connection 680 is closed. It is also envisioned that the gap distance between the two jaw members 110 and 120 may be controlled at the gap connection 680. More particularly, the gap connection 680 may be dimensioned such that the jaw members 110 and 120 remain a specific distance "G" relative to one another (See FIG. 6) during sealing. Preferably the separation distance during sealing or the gap distance "G" is within the range of about 0.001 inches (~0.03 millimeters) to about 0.006 inches (~0.016 millimeters).

It is also envisioned that the electrical connection may be completed through the ratchet mechanism 30. More particularly, the second electrical potential may be transmitted across the two shafts 12*a* and 12*b* by engagement of the two ratchet interfaces 30*a* and 30*b*. Although not shown in this particular figure, the ratchet interfaces 30*a* and 30*b* may include one or more electrical contact points which transmit the electrical potential when engaged. It is also envisioned that the interfaces 30*a* and 30*b* may include resistive coatings or resistive elements (not shown) which vary the given electrical potential across the shafts 12*a* and 12*b* as a function of the specific closure force of the ratchet 30. For example, it is contemplated that the successive interfacing ratchet positions may include a range of electrical potentials which vary depending upon the closure force between jaw members 110 and 120 to control the sealing process to between certain predetermined or ideal sealing parameters depending upon a particular purpose (e.g., varying tissue types). Alternatively, the interfacing portions 30*a* and 30*b* of the ratchet 30 may include selectively interchangeable inserts (not shown) which vary the electrical potential across the shafts 12*a* and 12*b* and to the jaw members 110 and 120 to control the sealing process for specific tissue types.

Figure 10B:
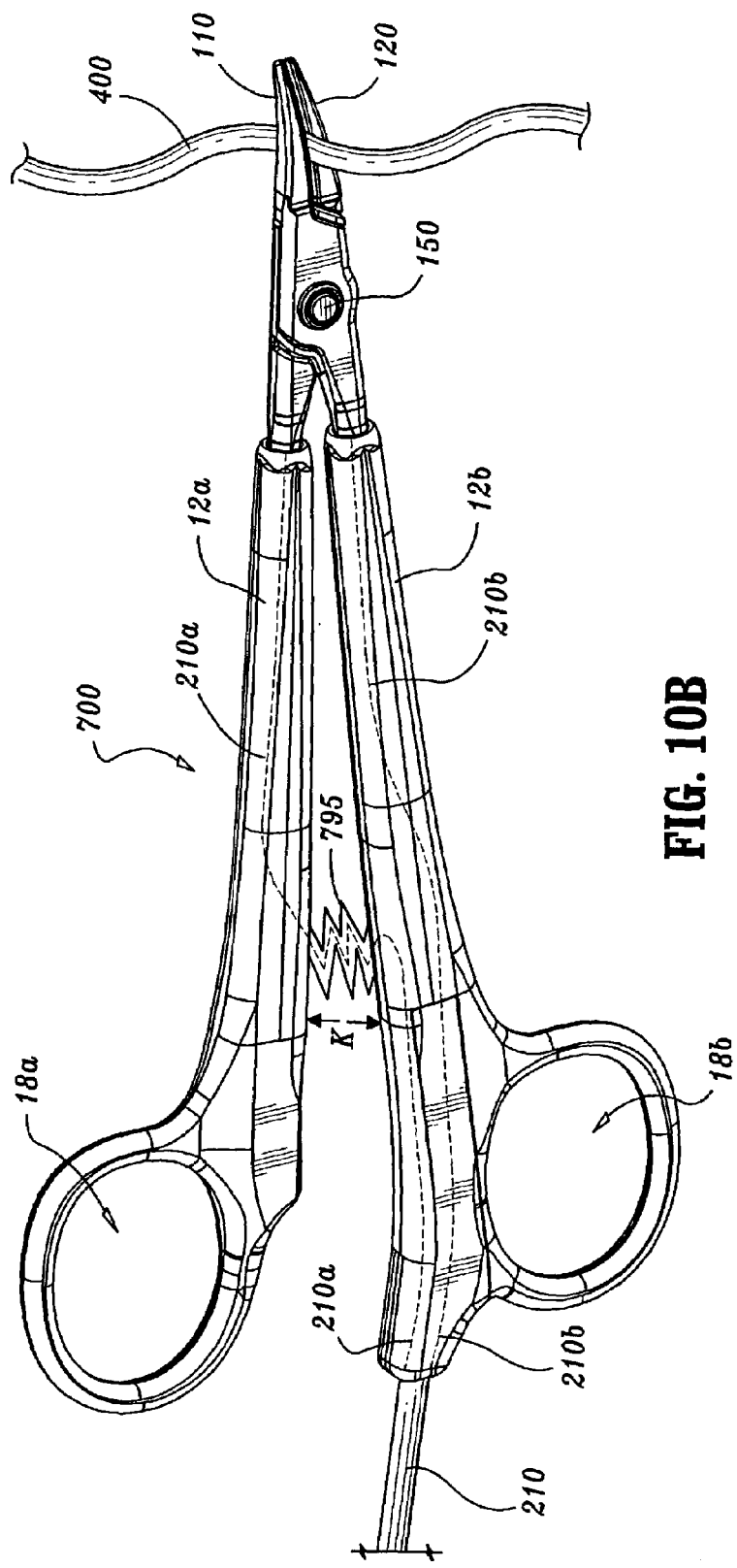
FIG. 10B is a side perspective view of another embodiment according to the present disclosure showing a flex relief member which biases the jaw members in an open configuration.

FIG. 10B shows another forceps design according to the present disclosure wherein forceps 700 includes a flex relief 795 disposed between the two shaft members 12*a* and 12*b*. The second electrical potential is carried across the two shafts 12*a* and 12*b* through the flex relief member 795 which, as described above, reduces the chances of inadvertently tangling the power cables during use. It is envisioned that the flex relief member 795 may be spring-biased (spring force "K") to maintain the forceps 700 in an open configuration when not in use.

Figure 11:
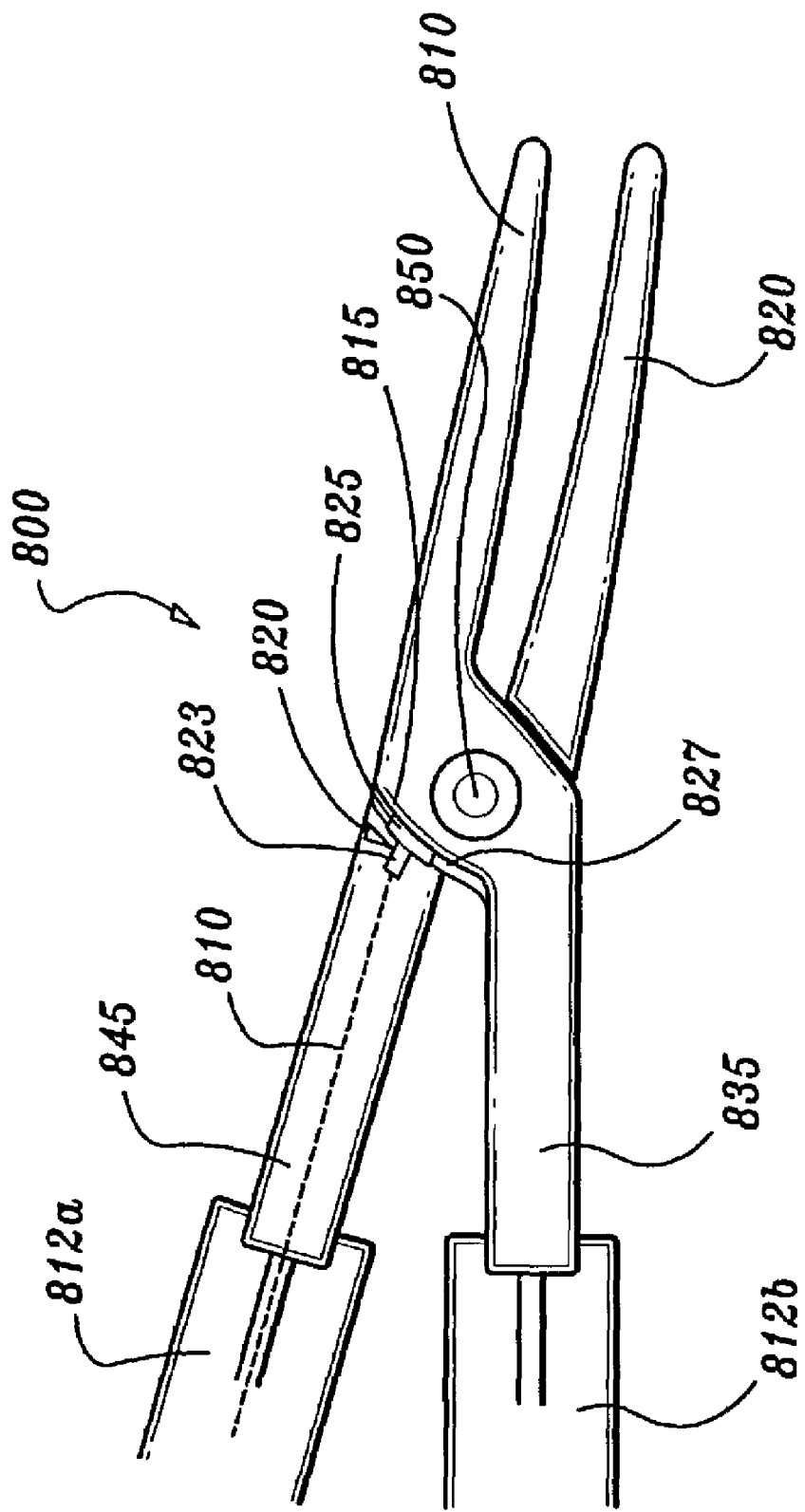
FIG. 11 is a side view of another embodiment according to the present disclosure showing a pin contact in running contact with a proximal end of one of the jaw members.

FIG. 11 shows yet another possible alternate design of the present disclosure which includes a forceps 800 having pin-like terminal connector 820 which attaches to one of the jaw members, e.g., jaw member 810. More particularly, each jaw member 810 and 820 includes a proximal end 845 and 835, respectively, which affixes to a corresponding end of one of the two shafts, i.e., proximal end 845 attaches to shaft 812*a* and proximal end 835 attaches to shaft 812*b*. Lead 810 extends through shaft 812*a* and includes a terminal end 820 which engages the proximal end of jaw member 810. Preferably, the terminal end 820 includes a t-shaped pin 825 which transfers the electrical potential from the lead to the jaw member 810. More particularly, the t-shaped pin 825 is dimensioned to ride within a slot 827 disposed in the proximal or rear end 815 of jaw member 810 during pivotal movement of the jaw member 810 and 820 relative to one another. As can be appreciated, the unique slot 827 and pin 825 arrangement of the connection wedges the pin 825 against the proximal end 815 of the jaw member 810 to provide electrical continuity through the entire pivoting motion of the jaw members 810 and 820. Preferably, the concave dimension (inner radius) of the pin 825 matches the convex or arcuate dimensions of the outer edge (outer radius) of the proximal end 815 to assure smooth pivoting operation of the jaw members 810 and 820 through the entire range of motion without loss of electrical continuity.

From the foregoing and with reference to the various figure drawings, those skilled in the art will appreciate that certain modifications can also be made to the present disclosure without departing from the scope of the present disclosure. For example, it may be preferable to include a tang which facilitates manipulation of the forceps 10 during surgery.

Moreover, although the electrical connections are preferably incorporated with the bottom shaft 12*b* and the instrument is intended for right-handed use, it is contemplated the electrical connections may be incorporated with the other shaft 12a depending upon a particular purpose and/or to facilitate manipulation by a left-handed user.

It is also contemplated that a shrink tube may be employed over the proximal connector 80 and/or the other various solder or crimp connections 85, 87 and 89 associated with the proximal connector 80 interface with lead wire 210b. This provides additional insulating protection during assembly. An insulative sheath may also be used to cover the end effector assembly 100 or the outer surfaces (non-opposing surfaces) of the jaw members 110 and 120.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue 400 grasped between the jaw members 110 and 120. The sensor or feedback mechanism may also measure the impedance across the tissue during sealing and provide an indicator (visual and/or audible) that an effective seal has been created between the jaw members 110 and 120.

Experimental results in animal studies suggest that the magnitude of pressure exerted on the tissue by the seal surfaces 112 and 122 is important in assuring a proper surgical outcome. Tissue pressures within a working range of about 3 kg/cm$^2$ to about 16 kg/cm$^2$ and, preferably, within a working range of 7 kg/cm$^2$ to 13 kg/cm$^2$ have been shown to be effective for sealing arteries and vascular bundles. Tissue pressures within the range of about 4 kg/cm$^2$ to about 6.5 kg/cm$^2$ have proven to be particularly effective in sealing arteries and tissue bundles.

In one embodiment, the shaft portions are manufactured such that the spring constant of the shaft portions 12a and 12b, in conjunction with the placement of the ratchet interfaces 32a and 32b, will yield pressures within the above working range. In addition, the successive positions of the ratchet interfaces increase the pressure between opposing seal surfaces 112 and 122 incrementally within the above working range.

It is envisioned that the outer surface of the jaw members 110 and 112 may include a nickel-based material, coating, stamping, metal injection molding which is designed to reduce adhesion between the jaw members 110, 112 (or components thereof) with the surrounding tissue during activation and sealing. Moreover, it is also contemplated that other components such as the shaft portions 12a, 12b and the ring holes 18a, 18b may also be coated with the same or a different "non-stick" material. Preferably, the non-stick materials are of a class of materials that provide a smooth surface to prevent mechanical tooth adhesions.

It is also contemplated that the tissue sealing surfaces, e.g., 112 and 122 of the jaw members 110 and 120 (or the other references tissue sealing surfaces shown in the other figures, e.g., 145', 151', 251', 350a, 350b, 450, 550a and 550b) can be made from or coated with these non-stick materials. When utilized on the sealing surfaces 112 and 122, these materials provide an optimal surface energy for eliminating sticking due in part to surface texture and susceptibility to surface breakdown due electrical effects and corrosion in the presence of biologic tissues. It is envisioned that these materials exhibit superior non-stick qualities over stainless steel and should be utilized on the forceps 10 in areas where the exposure to pressure and electrosurgical energy can create localized "hot spots" more susceptible to tissue adhesion. As can be appreciated, reducing the amount that the tissue "sticks" during sealing improves the overall efficacy of the instrument.

The non-stick materials may be manufactured from one (or a combination of one or more) of the following "non-stick" materials: nickel-chrome, chromium nitride, MedCoat 2000 manufactured by The Electrolizing Corporation of OHIO, Inconel 600 and tin-nickel. For example, high nickel chrome alloys and Ni200, Ni201 (~100% Ni) may be made into electrodes or sealing surfaces by metal injection molding, stamping, machining or any like process.

The Inconel 600 coating is a so-called "super alloy" which is manufactured by Special Metals, Inc. located in Conroe Tex. The alloy is primarily used in environments which require resistance to corrosion and heat. The high Nickel content of Inconel makes the material especially resistant to organic corrosion. As can be appreciated, these properties are desirable for bipolar electrosurgical instruments which are naturally exposed to high temperatures, high RF energy and organic matter. Moreover, the resistivity of Inconel is typically higher than the base electrode material which further enhances desiccation and seal quality.

As mentioned above, the tissue sealing surfaces 112 and 122 may also be "coated" with one or more of the above materials to achieve the same result, i.e., a "non-stick surface". For example, Nitride coatings (or one or more of the other above-identified materials) may be deposited as a coating on another base material (metal or nonmetal) using a vapor deposition manufacturing technique.

One particular class of materials disclosed herein has demonstrated superior non-stick properties and, in some instances, superior seal quality. For example, nitride coatings which include, but are not limited to: TiN, ZrN, TIAIN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A bipolar electrosurgical instrument for use in open surgery for sealing and cutting tissue, comprising:

first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween, each of said jaw members including a channel extending from a proximal end of the jaw member to the distal end of the jaw member and each of the jaw members including an electrically conductive sealing surface;

the jaw members being adapted to connect to a source of electrosurgical energy having first and second electrical potentials, the first electrical potential being connected to one of the jaw members and a second electrical potential being connected to the other of the jaw members such that the jaw members are capable of selectively conducting energy through tissue held therebetween to effect a seal;

a knife disposed within each of said channels between the first and second jaw members, said knife being selectively translatable within each of said channels from a first position proximal to tissue grasped between said jaw members to a distal position to sever tissue held between said jaw members; and at least one of the jaw members including at least one non-conductive stop member operatively associated with said electrically conductive sealing surface to control the distance between opposing electrically conductive sealing surfaces during the sealing process when tissue is held therebetween.

2. A bipolar electrosurgical instrument for use in open surgery according to claim 1 further comprising a control rod for remotely actuating said knife.

3. A bipolar electrosurgical instrument for use in open surgery according to claim 2 wherein said control rod is disposed along an outer periphery of one of the first and second shafts.

4. A bipolar electrosurgical instrument for use in open surgery according to claim 2 wherein the control rod is disposed through a spacer within said pivot.

5. A bipolar electrosurgical instrument for use in open surgery according to claim 1 wherein the stop member controls the distance between opposing electrically conductive sealing surfaces when tissue is held therebetween within the range of about 0.001 inches to about 0.006 inches.

6. A bipolar electrosurgical instrument for use in open surgery according to claim 1 wherein the knife is made from a non-conductive material.

7. A bipolar electrosurgical instrument for use in open surgery according to claim 1 wherein the knife is made from a conductive material and is adapted to be connected to the electrosurgical energy source.

8. A bipolar electrosurgical instrument according to claim 7 further comprising a non-stick coating disposed on the electrically conductive sealing surfaces.

9. A bipolar electrosurgical instrument according to claim 8 wherein the non-stick coating is selected from a group of materials consisting of: nitrides and nickel/chrome alloys.

10. A bipolar electrosurgical instrument according to claim 8 wherein the non-stick coating includes one of TiN, ZrN, TiAlN, CrN, nickel/chrome alloys with a Ni/Cr ratio of approximately 5:1, Inconel 600, Ni200 and Ni201.

11. A bipolar electrosurgical instrument according to claim 1 further comprising a ratchet disposed on the first shaft and a complementary interlocking mechanical interface disposed on the second shaft, said ratchet and complementary interlocking mechanical interface providing at least one interlocking position to maintain a closure pressure in the range of about 3 kg/cm$^2$ to about 16 kg/cm$^2$ between the jaw members.

12. A bipolar electrosurgical instrument for use in open surgery for sealing and cutting tissue, comprising:

first and second shafts each having a jaw member extending from a distal end thereof and a handle disposed at a proximal end thereof for effecting movement of the jaw members relative to one another about a pivot from a first position wherein the jaw members are disposed in spaced relation relative to one another to a second position wherein the jaw members cooperate to grasp tissue therebetween, each of the jaw members includes an electrically conductive sealing surface;

the jaw members being adapted to connect to a source of electrosurgical energy having first and second electrical potentials, the first electrical potential being connected to one of the jaw members and a second electrical potential being connected to the other of the jaw members such that the jaw members are capable of selectively conducting energy through tissue held therebetween to effect a seal;

one of said jaw members including a recess at a proximal end thereof for housing a knife therein, said recess having a cam-like profile such that selective, distal movement of said knife deflects said knife into and through tissue held between jaw members; and at least one of the jaw members includes at least one non-conductive stop member operatively associated with said electrically conductive sealing surface to control the distance between opposing electrically conductive sealing surfaces during the sealing process when tissue is held therebetween.

13. A bipolar electrosurgical instrument for use in open surgery according to claim 12 including a knife operatively associated with said recess wherein said knife is made from a non-conductive material.

14. A bipolar electrosurgical instrument for use in open surgery according to claim 12 including a knife operatively associated with said recess wherein said knife is made from a conductive material and is connected to the electrosurgical energy source.

15. A bipolar electrosurgical instrument for use in open surgery according to claim 12 wherein the at least one non-conductive stop member controls the distance between opposing electrically conductive sealing surfaces when tissue is held therebetween within the range of about 0.001 inches to about 0.006 inches.

16. A bipolar electrosurgical instrument according to claim 12 further comprising a non-stick coating disposed on the electrically conductive sealing surfaces.

17. A bipolar electrosurgical instrument according to claim 16 wherein the non-stick coating is selected from a group of materials consisting of: nitrides and nickel/chrome alloys.

18. A bipolar electrosurgical instrument according to claim 16 wherein the non-stick coating includes one of TiN, ZrN, TiAlN, CrN, nickel/chrome alloys with a Ni/Cr ratio of approximately 5:1, Inconel 600, Ni200 and Ni201.

19. A bipolar electrosurgical instrument according to claim 12 further comprising a ratchet disposed on the first shaft and a complementary interlocking mechanical interface disposed on the second shaft, said ratchet and complementary interlocking mechanical interface providing at least one interlocking position to maintain a closure pressure in the range of about 3 kg/cm$^2$ to about 16 kg/cm$^2$ between the jaw members.

* * * * *